US009456991B2

(12) United States Patent
Baes et al.

(10) Patent No.: US 9,456,991 B2
(45) Date of Patent: Oct. 4, 2016

(54) GELATIN/ALGINATE DELAYED RELEASE CAPSULES COMPRISING OMEGA-3 FATTY ACIDS, AND METHODS AND USES THEREOF

(71) Applicant: Erik K Baes, Cardiff (GB)

(72) Inventors: Erik Karel Baes, Cardiff (GB); Ida Marie Wold, Oslo (NO)

(73) Assignee: Erik Baes, Cardiff (GB)

( * ) Notice: Subject to any disclaimer, the term of this patent is extended or adjusted under 35 U.S.C. 154(b) by 0 days.

(21) Appl. No.: 14/310,041

(22) Filed: Jun. 20, 2014

(65) Prior Publication Data

US 2015/0004226 A1    Jan. 1, 2015

Related U.S. Application Data

(63) Continuation-in-part of application No. PCT/IB2012/003014, filed on Dec. 21, 2012.

(60) Provisional application No. 61/579,374, filed on Dec. 22, 2011, provisional application No. 61/710,483, filed on Oct. 5, 2012, provisional application No. 61/718,950, filed on Oct. 26, 2012.

(51) Int. Cl.
*A61K 9/50* (2006.01)
*A61K 9/52* (2006.01)
*A61K 9/48* (2006.01)
(Continued)

(52) U.S. Cl.
CPC ........... *A61K 9/4825* (2013.01); *A61K 9/4816* (2013.01); *A61K 9/5036* (2013.01); *A61K 9/5057* (2013.01); *A61K 31/05* (2013.01); *A61K 31/202* (2013.01); *A61K 31/232* (2013.01); *A61K 31/355* (2013.01); *A61K 31/375* (2013.01); *A61K 31/557* (2013.01); *A61K 45/06* (2013.01); *A61K 35/60* (2013.01)

(58) Field of Classification Search
CPC ............. A61K 9/4825; A61K 9/4816; A61K 9/5036; A61K 9/5057; A61K 31/557; A61K 31/232; A61K 31/05; A61K 31/355; A61K 31/375; A61K 31/202
See application file for complete search history.

(56) References Cited

U.S. PATENT DOCUMENTS 470,883 A    3/1892    Vanstone
4,900,571 A    2/1990    Kammuri et al.
(Continued)

FOREIGN PATENT DOCUMENTS

CN    1846716 A    10/2006
CN    101559045 A    10/2009
(Continued)

OTHER PUBLICATIONS

Reich. Formulation and physical properties of soft capsules. 2004, Edited Podzeck and Jones. pp. 201-212.*
(Continued)

*Primary Examiner* — Lakshmi Channavajjala
(74) *Attorney, Agent, or Firm* — Finnegan, Henderson, Farabow, Garrett & Dunner, LLP

(57) ABSTRACT

The present disclosure relates to delayed release capsules and methods of manufacturing the capsules. The capsules comprise a capsule shell comprising a combination of gelatin and alginate, wherein the capsule shell encapsulates or is filled with at least one agent, and the delayed release capsules are chosen from soft capsules and hard capsules.

24 Claims, 3 Drawing Sheets

(51) Int. Cl.
| | |
|---|---|
| *A61K 45/06* | (2006.01) |
| *A61K 31/05* | (2006.01) |
| *A61K 31/202* | (2006.01) |
| *A61K 31/232* | (2006.01) |
| *A61K 31/355* | (2006.01) |
| *A61K 31/375* | (2006.01) |
| *A61K 31/557* | (2006.01) |
| *A61K 35/60* | (2006.01) |

(56) References Cited

U.S. PATENT DOCUMENTS

| | | | |
|---|---|---|---|
| 4,975,040 | A | 12/1990 | Kammuri et al. |
| 5,882,715 | A | 3/1999 | Nielsen et al. |
| 6,030,641 | A | 2/2000 | Yamashita et al. |
| 6,245,811 | B1 | 6/2001 | Horrobin et al. |
| 6,783,770 | B2 | 8/2004 | Angel et al. |
| 8,609,138 | B2 | 12/2013 | Fujii et al. |
| 2003/0166508 | A1 | 9/2003 | Zhang |
| 2003/0175335 | A1 | 9/2003 | Scott et al. |
| 2004/0254357 | A1 | 12/2004 | Zaloga et al. |
| 2007/0082046 | A1 | 4/2007 | Chidambaram et al. |
| 2007/0098786 | A1 | 5/2007 | Chidambaram et al. |
| 2009/0061048 | A1 | 3/2009 | Kohane et al. |
| 2009/0074855 | A1 | 3/2009 | Xie et al. |
| 2009/0117172 | A1 | 5/2009 | Rogers et al. |
| 2012/0301546 | A1* | 11/2012 | Hassan .................. 424/465 |

FOREIGN PATENT DOCUMENTS

| | | |
|---|---|---|
| CN | 101628117 A | 1/2010 |
| CN | 102198115 A | 9/2011 |
| EP | 0118240 A2 | 9/1984 |
| EP | 0888778 A1 | 1/1999 |
| EP | 1112740 A1 | 7/2001 |
| JP | 58-194810 A2 | 11/1983 |
| JP | 61-126016 | 6/1986 |
| JP | 1-313421 A | 12/1989 |
| JP | 04207352 A | 1/1992 |
| JP | 4-36159 | 2/1992 |
| JP | 5-32543 | 2/1993 |
| JP | 5-245366 | 9/1993 |
| JP | 5-304906 | 11/1993 |
| JP | 11-76369 | 3/1999 |
| JP | 11-302158 | 11/1999 |
| JP | 3605360 A | 10/2004 |
| JP | 2009-185022 A | 8/2009 |
| JP | 2009-196961 A | 9/2009 |
| WO | 0170385 A2 | 9/2001 |
| WO | 03084516 A1 | 10/2003 |
| WO | 2006117675 A2 | 11/2006 |
| WO | 2007075475 A2 | 7/2007 |
| WO | 2007098612 A1 | 9/2007 |
| WO | 2009024376 A1 | 2/2009 |
| WO | 2010029433 A1 | 3/2010 |
| WO | 2011100935 A1 | 8/2011 |
| WO | 2012017326 A2 | 2/2012 |
| WO | 2013093630 A2 | 6/2013 |

OTHER PUBLICATIONS

Francis, "Wiley Encyclopedia of Food Science and Technology", Gelatin, 2nd ed., John Wiley & Sons, pp. 1183-1188, (2000).

Leuenberger, "Investigation of viscosity and gelatin properties of different mammalian and fish gelatins", Food Hydrocolloids, vol. 5, No. 4, pp. 353-361, (1991).

Smidsrod, et al., "Alginate as immobilization matrix for cells", TIBTECH, vol. 8, pp. 71-78, (Mar. 1990).

Remminghorst, et al., "Bacterial alginates: from biosynthesis to applications", Biotechnol Lett, vol. 28, pp. 1701-1712, (2006).

Gullapalli, "Soft Gelatin Capsules (Softgels)", Journal of Pharmaceutical Sciences, vol. 99, No. 10, pp. 4107-4748, (Oct. 2010).

Podczeck, et al., "Structure of Collagen", Pharmaceutical Capsules, Second Edition, pp. 24-25, (2004).

Dong, et al., "Alginate/gelatin blend films and their properties for drug controlled release", Journal of Membrane Science, www.sciencedirect.com; vol. 280, pp. 37-44, (2006).

Gelatin Manufacturers Institute of America, "Gelatin Handbook" pp. 1-26, (2012).

Narayani, et al., "Polymer-coated gelatin capsules as oral delivery devices and their gastrointestinal tract behaviour in humans", J. Biomatter, Sci, Polymer Edn, vol. 7, No. 1, pp. 39-48, (1995).

Picard, "Gelatin-Polysaccharide Mixed Biogels: Enzyme-Catalyzed Dynamics and IPNs", Macromol. Symp., pp. 291-292, 337-344, (2010).

Rosellini, et al., "Preparation and characterization of alginate/gelatin blend films for cardiac tissue engineering", pp. 447-453, (Sep. 25, 2007).

Shi, et al., "Preparation and characterization of novel sinomenine microcapsules for oral controlled drug delivery", Drug Development and Industrial Pharmacy, 36(4), pp. 482-489, (2010).

Smith, et al., "Polymer film formulations for the preparation of enteric pharmaceutical capsules", Journal of Pharmacy and Pharmacology pp. 167-172, (2010).

Sriamornsak, et al., "Modification of Theophylline Release With Alginate Gel Formed in Hard Capsules", AAPS PharmSciTech, 8 (3) Article 51, pp. El-E8, (2007).

Wang, et al., "Study on the Blend Film Prepared by Alginate and Gelatin", Advanced Materials Research vols. 201-203, pp. 2879-2882, (2011).

Xiao, et al., "Blend Films from Sodium Alginate and Gelatin Solutions", J. Macromol. Sci., Pure Appl. Chem. A38(3), pp. 317-328, (2001).

Fan, et al., "Importance of Dietary y-Linolenic Acid in Human Health and Nutrition", Recent Advances in Nutritional Science, pp. 1411-1414, (Jun. 18, 1998).

Reich, "Formulation and physical properties of soft capsules", Chapter 11, pp. 201-212, (2000).

Venkataram, et al., "Indomethacin sustained release from alginate-gelatin or pectin-gelatin coacervates", International Journal of Pharmaceutics 126, pp. 161-168, (1995).

International Preliminary Report on Patentability in International Application No. PCT/IB2012/003014 dated Jun. 3, 2014.

* cited by examiner

Encapsulation machine production diagram

GELATIN/ALGINATE DELAYED RELEASE CAPSULES COMPRISING OMEGA-3 FATTY ACIDS, AND METHODS AND USES THEREOF

FIELD

The present disclosure relates generally to gelatin/alginate capsules and methods of manufacturing such capsules. The capsules are suitable for pharmaceutical, nutritional, and food supplement applications. The present disclosure further relates to a delayed release capsule comprising a capsule shell comprising a combination of gelatin and alginate, wherein the capsule shell encapsulates or is filled with at least one agent and the delayed release capsule is chosen from a soft capsule, a hard capsule, a macrocapsule or a microcapsule. The at least one agent may, for example, comprise a fatty acid oil mixture and at least one salicylate.

BACKGROUND

Gelatin capsules have been used in the formulation of pharmaceuticals and food products. Gelatin has good availability, low cost, and no toxicity. Gelatin, however, is soluble in acidic media and hence not stable in gastric fluid. A few examples of gelatin capsules are discussed below.

WO 2007/098612 A1 discloses gastric-resistant gelatin compositions for use in the preparation of dosage forms, comprising modified gelatin with additional functional groups such as carboxylate groups or acyl groups and further addition of sodium alginate and fatty acid derivatives. The modified gelatin is used in normal softgel and hard gelatin capsule production processes. However, the reaction rate and viscosity of the modified gelatin is not easy to control.

WO 2009/024376 discloses a microcapsule for immobilizing organic or inorganic solids, lipophilic compounds, lipids or microorganisms for use in food additives, or as dietary supplements based on a spherical matrix encapsulation using alginate as the substance. The capsule comprises additional adjuncts and stabilizers in the alginate matrix. The immobilized ingredients are released after ingestion of the capsule only after passing through the stomach into the duodenum, and are protected from the prior digestive effects of the stomach. The capsules of WO 2009/024376 are prepared by complex mixing and spray drying or formation of beadlets, with collection of the particles from a $CaCl_2$ bath, followed by drying.

WO 2010/029433 discloses capsules comprising at least one oily phase that comprises a fatty acid oil mixture and at least one surfactant in an alginate capsule formulation. It is mentioned that other polymers, e.g. gelatin, might be present in the capsule shell. The shell of the capsules of WO 2010/029433 is thinner compared to gelatin capsules, thereby allowing a larger amount of material to be encapsulated. Furthermore, it is stated that alginate capsules may offer several benefits over gelatin capsules with regard to temperature and humidity stability, decrease in gastrointestinal reflux symptoms, as well as no need for testing for bovine spongiform encephalopathy (BSE). However, the production of the capsules of WO 2010/029433 is disadvantageous as inter alia it requires large amounts of water to wash the capsules, in order to remove the excess $CaCl_2$.

WO 2007/075475 discloses a capsule where the shell contains a gastric resistant natural polymer, a film forming natural polymer and optionally a gelling agent, where the gastric resistant polymer is a polysaccharide, such as pectin and pectin like materials. The film forming composition can be used to prepare softgel and hard gelatin capsules, where the fill material can be a liquid, a semi-solid or a solid tablet. The gastric resistant shell formulation can be "gelled" with the addition of $CaCl_2$ and $MgCl_2$. When preparing the gelatin/pectin formulation, there is a substantial increase in viscosity of the shell formulation, especially after adding the Ca chloride ($CaCl_2$) and Mg chloride ($MgCl_2$). However, this increase in viscosity is a limiting factor in the production of softgel capsules and the formulation has to be diluted with more water in order to bring it back into a workable range. The addition of additional water decreases the oxygen barriers properties of the shell substantially and renders the shell more fragile during manufacturing. The excess of water has to be evaporated during the drying process; drying takes longer and the active ingredients in the fill formulation may be exposed for a longer period of time to the additional water that will migrate into the fill formulation.

JP58194810A2 describes a miniature capsule with a size smaller than 5 mm, composed of gelatin and a polyhydric alcohol, where the surface of the capsule is coated with a powder, such as $CaCl_2$ and covered with another coat of methoxy pectin or sodium alginate. The powder reacts with the polysaccharide and renders it insoluble in acid media. The difficulty in this process is applying the powder uniformly over the surface of the miniature capsules and applying a water based coating to the surface. Since the second coat contains a very big amount of water to dissolve the pectin or alginate, the water will penetrate the gelatin shell and will affect is physical characteristics and protective properties, as well as require another process to dry the capsules.

EP 0 888 778 A1 describes a dosage form intended to deliver a drug in the colon, without disintegrating in the upper intestinal tract. The dosage form consists of a film around an existing product or a shell containing the active ingredients. The film formulation is based on the interaction of gelatin with a polysaccharide, in this case a pectin. The film is rendered insoluble in the upper intestinal tract, by reacting the pectin with calcium salts and cross-linking the gelatin component with strong aldehydes. Other polysaccharides are mentioned, including alginate. This formulation suggested in this particular application has extremely wide ranges for the pectin and the gelatin, ranging from 1 to 99% of the composition. Such ranges would not be useable in an industrial application. Furthermore the gelatin is cross linked optionally with strong aldehydes, including formaldehyde, in order to protect it from the upper intestinal tract enzyme, otherwise the gelatin will be degraded by proteolitic enzymes. It is known that cross-linking of gelatin with strong aldehydes causes the gelatin to become completely insoluble. The application of those aldehydes to the product, either in capsule form or as a coating presents several hazards to health.

JP 200919696 claims an enteric capsule comprising a film, wherein the film contains at least one kind selected from the group consisting of a water-soluble salt of alginic acid, gelatin, agar and curdlan. The film may further comprise at least one kind of gelling agent selected from the group consisting of gellan gum, carrageenan, pectin, xanthan gum, locust bean gum and tamarind seed gum, and additionally the film may further comprise a plasticizer. The capsule is prepared by dip coating to form a hard capsule. The film is said to comprise about 20-90% by weight of the alginate. However, according to the working examples alginate constitutes at least 50% by weight of the film and only hard capsules are prepared.

JP 1176369 discloses an enteric soft capsule prepared from sodium alginate having a viscosity of 50 to 400 cps (in 1% aqueous solution at 20° C.) with a soft capsule film base consisting of gelatin, preferably type B, and plasticizer as the main raw materials at 1 to 10% by weight with 100% by weight gelatin without using a bivalent cation for crosslinking and gelatinizing sodium alginate. However, this gelatin base is limited to the production of soft gels.

JP 2009185022 claims an enteric sustained-release soft capsule, wherein the soft capsule is formed by kneading gelatin, polyhydric alcohols as plasticizers, polysaccharides, alkali metal salts and water, wherein the polysaccharides are at least two kinds selected from carrageenan, agar, locus bean gum, guar gum, tamarind seed polysaccharide, pectin, xanthan gum, glucomannan, chitin, pullulan, alginic acid and alginic acid derivatives. The capsule comprises from 6-40% by weight of the at least two kinds of polysaccharide, wherein the alkali metal salt is preferably a calcium salt.

US 2007/098786 describes enteric valproic acid soft gelatin capsule, in which the fill material comprises valproic acid or divalproex sodium and, optionally, one or more excipients. The capsule shell is prepared from a mass comprising a film-forming polymer, an acid insoluble polymer, an aqueous solvent, and optionally a plasticizer. Suitable film-forming polymers include gelatin. Suitable acid-insoluble polymers include, e.g., acrylic-acid/methacrylic acid copolymers, alginic acid salts, etc. The acid-insoluble polymer is present in an amount from about 8% to about 20% by weight of the wet gel mass. The weight ratio of acid-insoluble polymer to film-forming polymer is from about 25% to about 50%. The aqueous solvent is water or an aqueous solution of alkalis. Suitable plasticizers include glycerin and triethylcitrate. A disadvantage is that enteric valproic acid soft gelatin capsules may be smaller in size than currently available enteric coated tablets.

The use and application of alginate in film-forming projects has not been widely explored. Reasons for this include the difficulty in finding a combination with other film-formers that can be applied in an industrial environment. The present disclosure provides for the use of alginates in film-forming applications and the conditions for their application.

SUMMARY

The present disclosure relates to delayed release capsules, using standard production processes for manufacturing with alternative materials and/or procedures developed.

In an embodiment, there is disclosed a delayed release capsule comprising: at least one agent encapsulated in a capsule shell, wherein the capsule shell comprises a type A gelatin, such as fish gelatin, bovine gelatin, pig gelatin, and mixtures thereof, having a viscosity below 4.2 mPa·sec and/or a bloom value below 290 g; and alginate, in an amount ranging from 0.5% to 10%, by weight of the gelatin, wherein the alginate has a viscosity ranging from 2 to 600 mPa·sec. In one embodiment of the delayed release capsule, when the alginate is a high G alginate, the viscosity of the alginate does not range from 45 mPa·sec to 420 mPa·sec.

In an embodiment, the delayed release capsule may be a sustained release capsule, a controlled release capsule, or a gastroresistant capsule.

The present disclosure is also directed to a method of manufacturing the delayed release capsules. In one embodiment, the method comprises using existing soft gelatin capsule or hard gelatin capsule production processes. These standard process allow the gelatin/alginate, which may include a plasticizer, to be cast onto cooling drum or molding pins and formed into ribbons or films and other ingredients which are applied by various means including lubricating rollers and whereby the standard industry lubricants are changed to a novel type allowing the application of water soluble ingredients to the capsule shell.

The accompanying drawings, which are incorporated in and constitute a part of this specification, illustrate one embodiment of the disclosure and together with the description, serve to explain the principles of the disclosure.

DESCRIPTION

Figure 1:
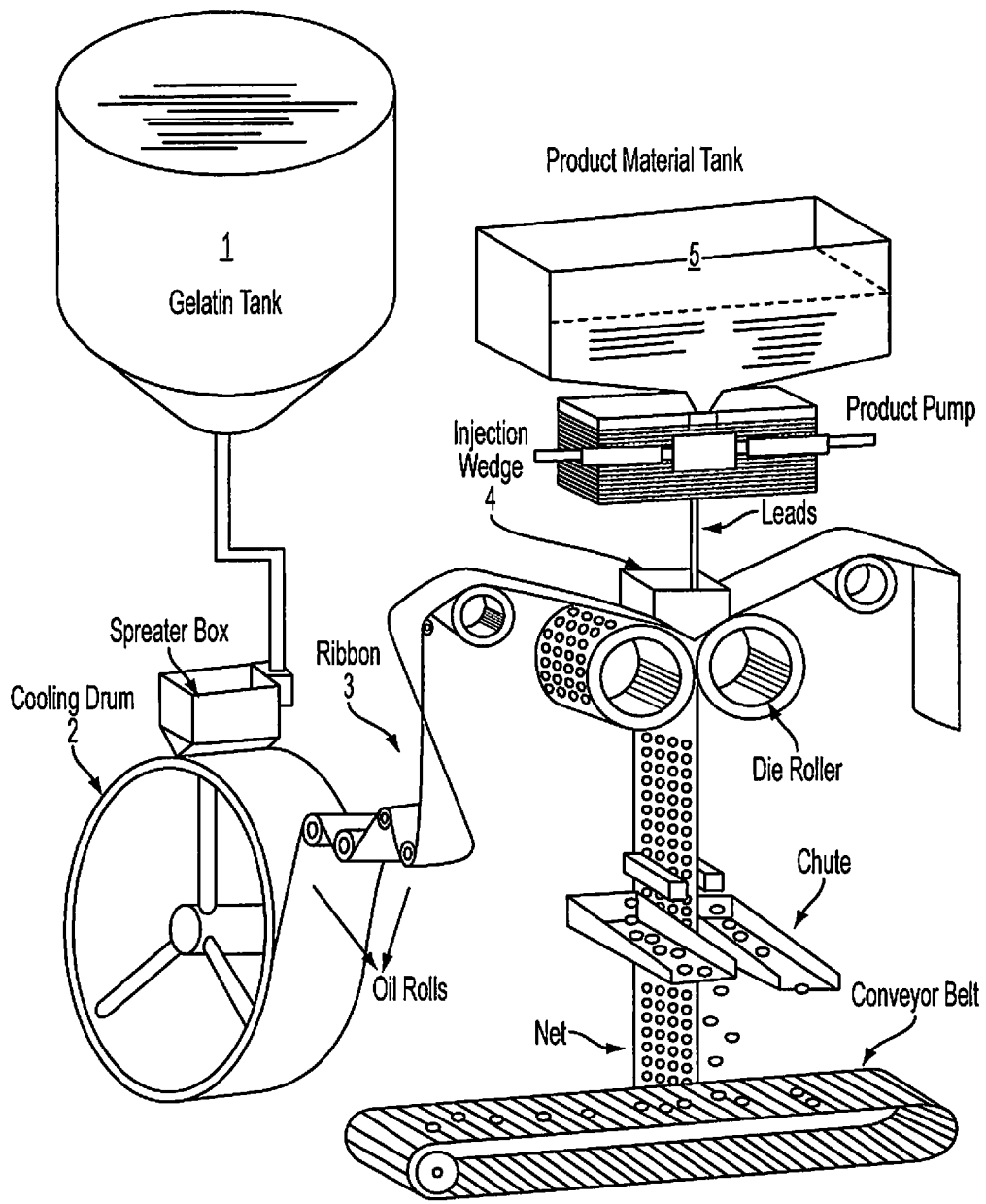
FIG. 1 is a depiction of a manufacturing process of softgels and SOFTLETS®.

Particular aspects of the disclosure are described in greater detail below. The terms and definitions as used in the present application and as clarified herein are intended to represent the meaning within the present disclosure. The patent and scientific literature referred to herein and referenced above is hereby incorporated by reference. The terms and definitions provided herein control, if in conflict with terms and/or definitions incorporated by reference.

The singular forms "a," "an," and "the" include plural reference unless the context dictates otherwise.

The terms "approximately" and "about" mean to be nearly the same as a referenced number of value. As used herein, the terms "approximately" and "about" should be generally understood to encompass ±15% of a specified amount, frequency, or value.

The present disclosure provides delayed release capsules of modified gelatin/alginate polymer resistant to gastric fluid to a degree that is controllable and thereby capable of delivering the active ingredient in the stomach or in the intestine by regulating the dissolution of the shell according to a set pH, thereby protecting the active ingredient against low pH values.

Additionally, the delayed release capsules can be produced by using a continuous existing production process of soft gelatin capsules ("softgels") or of hard gelatin capsules. A softgel is a pharmaceutical, nutritional, or other singular unit dosage form, in which the shell comprises a membrane of gelatin, polysaccharides, cellulose or derivatives and natural polymers and at least one plasticizer. In general, in softgels capsules, the gelatin has a viscosity of less then 18 mPoise, such as a maximum of 38 mPoise. The unit in softgel capsules may be filled with liquids, solutions, dispersions, suspensions, emulsions and/or other unit singular or multiple unit dosage forms. The products sold under the tradenames SOFTLETS® and UNIGEL™ are non-limiting examples of softgels. SOFTLETS® are film-enrobed unitary core products. A UNIGEL™ capsule is a soft gelatin capsule comprising a soft gelatin shell which encapsulates or is filled with a solid unit dosage form or multiple solid dosage forms in the form of beadlets or granules. For example, a UNIGEL™ capsule may resemble a softgel with a tablet or beadlets floating in the fill, as the capsule may be filled with solid core dosage forms and the normal softgel fill formulations.

In contrast, a hardshell typically does not contain a plasticizer but is pure gelatin. Hardshell capsules typically comprise telescoping two piece capsules, and have a bloom value of less than 220 g, and a viscosity such as a maximum of 42 mPoise.

The present disclosure can also provide new capsules comprising a gelatin/alginate polymer film which may or may not be cross-linked by $CaCl_2$, $MgCl_2$ or $ZnCl_2$, or other divalent salts, encapsulating at least one agent, such as an active pharmaceutical ingredient or nutritional or food supplement.

Capsule Compositions

The present disclosure is directed to a delayed release capsule comprising a capsule shell comprising a combination of: gelatin chosen from type A gelatin, or a combination of type A gelatin and type B gelatin, wherein the gelatin has a viscosity below 4.2 mPa·sec and/or a bloom value below 290 g; and alginate, in an amount ranging from 0.2% to 20%, such as from 0.5% to 10% by weight of the gelatin, wherein the alginate has a viscosity ranging from 2 mPa·sec to 600 mPa·sec; and wherein the capsule shell encapsulates or is filled with at least one agent and the delayed release capsule is chosen from a soft capsule and a hard capsule. In one embodiment, the viscosity of the alginate does not range from 45 mPa·sec to 420 mPa·sec when the alginate is a high G alginate.

In one embodiment, the capsule shell further comprises at least one cross-linking agent.

Gelatin

Gelatins are proteinaceous substances obtained from chemical-thermal extraction from the fibrous animal protein collagen. The capsule shell disclosed herein may, for example, comprise gelatin present in an amount ranging from about 32% to about 90%, relative to the weight of the capsule shell.

Gelatin Production

Two main gelatin extraction processes are used: lime and acid pre-treatment processes followed by hot water extraction. These processes give gelatin with different molecular weight distributions of the polypeptide chains, which in turn affects the viscosity, and a second property related to the film strength (capacity to reform 3-D collagen structures), called bloom value. Bloom Value, which is also known as "bloom strength" is discussed in more detail below.

Depending on the type of pretreatment process and the extraction procedure, the range of available viscosities of a $6^{2/3\%}$ solution at 60° C. will range from 1.5 to 5.0 mPa·sec. The gelatin bloom strength, according to the type and origin of the raw material and the method of extraction, will range from 40 g to 450 g bloom.

Type A and B Gelatin

Gelatin is produced by destruction of secondary and, to a certain extent, higher structures in collagen (Babel, 1996). Gelatins may be of type A or B, depending on the kind of pre-treatment to which the collagenous tissue has been subjected. There are several processes by which collagen is processed to gelatin, but the two most common, as noted above, are the acidic and alkaline pre-treatments followed by extractions. Type A gelatin is obtained from animal skin, usually porcine skin, or hide, or from bovine, pork, fish and other animals, pre-treated with acid. Type B gelatin is derived from collagenous raw materials subjected to alkaline pre-treatment. The alkali process is mainly used on bovine hide and bone collagen sources where the animal is relatively old at slaughter (FRANCIS, F. J. 1999. Gelatin. *Wiley Encyclopedia of Food Science and Technology*. 2*nd* ed.: John Wiley & Sons).

In the delayed release capsules disclosed herein, the gelatin, for example, may be chosen from porcine bone, porcine skin, and combinations thereof. The gelatin preferably comprises type A gelatin, such as fish gelatin. Type A gelatin is preferred due to its lower viscosity compared to type B gelatin at equivalent bloom values. In at least one embodiment, the gelatin comprises both type A and type B gelatins.

In at least one embodiment of the delayed release capsules disclosed herein, the gelatin comprises type A gelatin having a viscosity ranging from about 2.3 to about 3.5 mPa·sec and a bloom value ranging from about 150 g to about 250 g.

Bloom Strength

Bloom value (also called "bloom strength") is an indication of the gel strength, and measured as the amount of weight required to depress a 6.66% gelatin solution that has been matured at 10° C. for 16 hours, with a standard plunger to a depth of 2 mm. Gel strength is directly proportional to bloom value, e.g., the higher the bloom value, the higher the gel strength. For more information, see FRANCIS, F. J. 1999. Gelatin. *Wiley Encyclopedia of Food Science and Technology*. 2*nd* ed.: John Wiley & Sons), which is incorporated by reference.

In another embodiment, the gelatin has a bloom value of below about 290 g, such as below 220 g, 200 9, or even below 190 g. In yet another embodiment, the gelatin has a bloom value ranging from about 60 to about 180, such as from about 140 to about 180.

Fish Gelatin

Gelatins from marine sources may have advantages compared to mammalian gelatins, such as lower gelling and melting temperatures (Johnson-Banks, 1990; LEUENBERGER, B. H. 1991. Investigation of viscosity and gelation properties of different mammalian and fish gelatins. *Food Hydrocolloids*, 5, 353-361). The fear of bovine spongiform encephalopathy (BSE) also favours the use of gelatin from fish for food, nutritional, and pharmaceutical applications. Moreover, vast amounts of by-products from the fish industry are discharged every year. This material could be utilized for gelatin production.

In at least one embodiment of the delayed release capsule disclosed herein, the capsule is a soft capsule, and the gelatin comprises fish gelatin.

Alginate

The delayed release capsules disclosed herein further comprise alginate in the capsule shell. As a non-limiting example, the alginate may be present in an amount ranging from about 0.2% to 20%, such as 0.5% to 10%, or from about 5% to about 10%, by weight of the gelatin.

The alginate in the capsule shell disclosed herein may, for example, be chosen from alginate with a high fraction of mannuronic acid residues (high M alginate) or alginate with a high fraction of guluronic acid residues (high G alginate). For instance, in at least one embodiment, the alginate is chosen from high M sodium alginate. In another embodiment the alginate is chosen from high G sodium alginate.

For example, in at least one embodiment, the alginate comprises high M alginate and the gelatin has a bloom value below about 220 g. In another embodiment, the alginate comprises high M alginate or high G alginate, and the M/G ratio are ranging from about 0.37 to about 3.08 (ref: http://www.fao.org/docrep/X5822E/x5822e04.htm).

Alginates are commonly found in brown seaweeds such as *Laminaria hyperborea, Laminaria digitata, Laminaria japonica, Ascophyllum nodosum*, and *Macrocystis pyrifera* (SMIDSRØD, O. & SKJÅK-BRÅK, G. 1990. Some bacterial species can also produce alginates with more defined chemical and physical properties, including the bacterial families of *Pseudomonas* and *Azotobacter* (REMMING-HORST, U. & REHM, B. 2006. Bacterial alginates: from biosynthesis to applications. *Biotechnology Letters*, 28, 1701-1712).

The alginate in the delayed release capsule disclosed herein may, for example, be chosen from sodium alginate, polyethylene glycol alginate, and mixtures thereof. For instance, in at least one embodiment, the gelatin comprises fish gelatin and the alginate comprises high M sodium alginate derived from seaweed.

The alginate typically used in capsules has a viscosity in a 1% solution of from 2.0 to 1000 mPa·sec at 20° C. In at least one example, the viscosity ranges from 2.0 to 600 mPa·sec. Both forms of predominantly M and G alginates can be used, representing a mannuronic to guluronic acid ratio of values ranging from about 3.0 to about 0.4, for example ranging from 0.9 to 1.5.

Thus, the delayed release capsules disclosed herein may, for example, comprise alginate comprising high M alginate having a viscosity above 420 mPa·sec, e.g. ranging from 420 to 600 mPa·sec or from 460 to 560 mPa·sec, or from 480 to 540 mPa·sec.

In at least one embodiment of the delayed release capsules disclosed herein, the alginate comprises a high M alginate having a viscosity ranging from 505 to 535 mPa·sec, such as high M alginate having a viscosity ranging from 510 to 530 mPa·sec. In a preferred embodiment, the alginate comprises high M alginate having a viscosity of 520 mPa·sec.

In another non-limiting example, the alginate may comprise high G alginate having a viscosity below 45 mPa·sec, below 40 mPa·sec, below 30 mPa·sec, or even a viscosity below 20 mPa·sec.

In another embodiment, in the case that the capsule shell further comprises at least one cross-linking agent, the alginate comprises a high G alginate having a viscosity of about 300 to 400 mPa·sec, such as, e.g. 340 mPas·sec.

Alginate/Gelatin Combination

The delayed release capsules disclosed herein comprise a combination of gelatin and alginate, resulting in a viscosity interaction, wherein the sum of the viscosities of a gelatin solution and an alginate solution is less than the viscosity of a solution in which both are dissolved. In at least one embodiment, an interaction parameter ranges in value from about 3.2 to about 6.0.

In at least one embodiment, the pH of the gelatin/alginate solution is adjusted to range from about 3.5 to about 5.0, such as from about 3.7 to about 4.5.

The delayed release capsules disclosed herein encompass various gelatin/sodium alginate combinations.

For example, gelatin can be replaced by from about 1% to about 10% low molecular weight (low viscous) "G" alginate having a viscosity below about 20 mPa·sec (1%, 20° C.) or about 1% to about 10% (medium viscous) "M" alginate having a viscosity of about 520 mPA·sec (1%, 20° C.). In other words, if a low viscous G alginate or medium viscous M alginate is used, then 1-10% of the gelatin weight in the formulation can be replaced with alginate.

As another example, gelatin can be replaced by from about 1% to about 5% medium molecular weight (medium viscous) "M" alginate. In still another example gelatin can be replaced by from about 5% to about 10% of (low viscous) "G" alginate having a viscosity below about 20 mPa·sec (1%, 20° C.).

In yet another example, gelatin can be replaced by from about 1 to about 5% "G" alginate having a viscosity below about 20 mPa·sec (1%, 20° C.). In yet another example gelatin can be replaced by from about 5% to about 10% of "M" alginate having a viscosity of about 520 mPa·sec.

In one embodiment, the delayed release capsule disclosed herein, comprises the gelatin chosen from type A porcine gelatin, wherein the gelatin has a viscosity below about 4.2 mPa·sec and/or a bloom value below 220 g, such as below 200 g, or even below 190 g. In this or other embodiments, the alginate may be present in an amount ranging from about 1% to about 10%, by weight of the gelatin, wherein the alginate is chosen from high M alginate having a viscosity of about 520 mPa·sec; and wherein the capsule shell encapsulates or is filled with at least one agent and the delayed release capsule is a soft capsule.

In another embodiment, the delayed release capsule disclosed herein, comprises the gelatin chosen from type A porcine gelatin, wherein the gelatin has a viscosity below about 4.2 mPa·sec and/or a bloom value below 220 g, such as below 200 g; and the alginate, in an amount ranging from about 1% to about 10%, by weight of the gelatin, wherein the alginate is chosen from high G alginate having a viscosity below about 45 mPa·sec; and wherein the capsule shell encapsulates or is filled with at least one agent and the delayed release capsule is a soft capsule; and wherein the shell further comprises at least one cross-linking agent, such as one comprising $CaCl_2$.

In another embodiment, the delayed release capsule disclosed herein, comprises an A type gelatin chosen from fish or porcine gelatin, wherein the gelatin has a viscosity below about 4.2 mPa·sec and/or a bloom value of about 180 g; and the alginate, in an amount ranging from about 1% to about 10%, by weight of the gelatin, wherein the alginate is chosen from high M alginate having a viscosity of about 520 mPa·sec; and wherein the capsule shell encapsulates or is filled with at least one agent and the delayed release capsule is a hard capsule.

Plasticizer

When the delayed release capsule disclosed herein comprises a soft capsule, the capsule shell of the delayed release capsule may further comprise at least one plasticizer. The at least one plasticizer may be chosen, for example, from glycerol, sorbitol, trehalose, sorbitan solutions, maltitol solutions, polyethylene glycol, propylene glycol, and mixtures thereof.

For example, in at least one embodiment, the at least one plasticizer comprises glycerol.

In at least one embodiment, the glycerol and the gelatin are present at a gelatin:glycerol ratio ranging from 1.4 to 5.

In at least one embodiment, the at least one plasticizer comprises glycerol and sorbitol present at a ratio ranging from 0.5 to 2.5, such as from 1 to 2.5, and the glycerol is present in an amount ranging from 5% to 40%, such as from 10% to 25%, relative to the weight of the capsule shell.

In at least one embodiment, the at least one plasticizer comprises glycerol and a sorbitan solution present at a ratio ranging from about 0.5 to about 4, and the glycerol is present in an amount ranging from 5% to 35%, such as from 10% to 35%, relative to the weight of the capsule shell.

In at least one embodiment, the at least one plasticizer comprises glycerol, a sorbitol solution, and a maltitol solution present at a ratio of about 1:3:1, and the glycerol is present in an amount ranging from 4% to 25%, relative to the weight of the capsule shell.

In at least one embodiment, the at least one plasticizer comprises glycerol and trehalose present at a ratio ranging from 1 to 5% of the weight of the gelatine, and the glycerol is present in an amount ranging from 3% to 25%, relative to the weight of the capsule shell.

In at least one embodiment, the at least one plasticizer comprises a sorbitan solution and a maltitol solution present at a ratio ranging from about 0.5 to about 2.0, and the maltitol is present in an amount ranging from 5% to 25%, relative to the weight of the capsule shell.

In at least one embodiment, the at least one plasticizer is chosen from polyethylene glycol and propylene glycol and is present in an amount ranging from about 1% to about 7.5%, relative to the weight of the capsule shell.

In at least one embodiment, the delayed release capsule is a soft capsule, and the alginate and gelatin combination and the plasticizer are present at a ratio ranging in value from about 1.4:1 to about 5:1.

In at least one embodiment, when the capsule shell comprises high G alginate, the shell further comprises at least one cross-linking agent.

Cross-Linking Agent

The membrane outer shell of the delayed release capsule disclosed herein may further comprise at least one cross-linking agent, such as divalent ions. When the at least one cross-linking agent comprises divalent ions, the alginate, for example, may comprise high G alginate.

In at least one embodiment, the at least one cross-linking agent may be chosen from $CaCl_2$, $MgCl_2$, $ZnCl_2$, calcium salts of food-grade organic acids, and any mixtures thereof. For example, in at least one embodiment, the at least one cross-linking agent is $CaCl_2$. In at least one embodiment, the at least one cross-linking agent may comprise cross-linking ions chosen from, for example, $Ca^{2+}$, $Sr^{2+}$, $Ba^{2+}$, $Zn^{2+}$, and $Mg^{2+}$.

Water

Where applicable, the total water present in the delayed release capsule disclosed herein is a combination of water supplied by the sorbitol solution, sorbitan solution, and/or maltitol solution, and any additional water added to reach the amount of water in the standard gelatin formulation. The "standard gelatin formulation" for softgels comprises gelatin, plasticizers, coloring and/or opacifying agents, flavoring agents, and water, in various proportions. For hard gelatin capsules, the "standard gelatin formulation" comprises gelatin, water, opacifying agents and/or coloring agents, and preservatives, if applicable.

Agent

The delayed release capsules disclosed herein encapsulate or are filled with at least one agent. In at least one embodiment, the at least one agent is dissolved, dispersed, or suspended in at least one oil of vegetable (such as algae), animal (such as fish), or unicellular origin, and obtained via a process chosen from pressing, extraction, purification, distillation, and chemical modification of a raw oil via esterification, hydrolisation, and/or hydrogenation.

In at least one embodiment, the at least one agent further comprises at least one suspending or solubilizing agent. The at least one suspending or solubilizing agent may, for example, be chosen from phospholipids, beeswax and other partially hydrogenated fatty acids, sorbitan esters of fatty acids, ethoxylated sorbitan esters of fatty acids, other surfactant agents, and mixtures thereof.

In at least one embodiment, the at least one agent is dissolved, dispersed, or suspended in polyethylene glycol of various molecular weights, mixtures of polyethelene glycols of various molecular weights, propylene glycol, and mixtures thereof.

In at least one embodiment, the at least one agent further comprises other ingredients to dissolve the at least one agent. For example, the other ingredients may be chosen from polyvinylpyrrolidone, ethyl alcohol, propyl alcohol, alpha tocopheryl polyethylene glycol succinate (Vitamin E TPGS), potassium or sodium hydroxides, other alkali or acidifying agents, and mixtures thereof.

In at least one embodiment the at least one agent further comprises at least one pharmaceutical active ingredient or a nutritional ingredient. By way of example might the nutritional ingredient may comprise a vitamin.

In at least one embodiment, the at least one agent is chosen from an active pharmaceutical ingredient, a nutritional or food supplement, and placebo material. For example, the capsule may be chosen from a pharmaceutical composition, a nutritional composition, a supplement composition, and dietary ingredients. As a further example, the capsule may be chosen from a pharmaceutical mixed fatty acid composition, an over-the-counter mixed fatty acid composition, and a nutritional or food supplement mixed fatty acid composition.

In at least one embodiment of the disclosure, the active pharmaceutical ingredient or nutritional or food supplement comprises at least one fatty acid oil mixture comprising at least one fatty acid in a form chosen from ethyl ester, mono-, di-, and triglycerides, free fatty acid, phospholipid, and combinations thereof. For example, the fatty acid oil mixture may comprise at least one fatty acid chosen from eicosapentaenoic acid (EPA) and docosahexaenoic acid (DHA). As used herein, the term "fatty acid oil mixture" includes fatty acids, such as unsaturated (e.g., monounsaturated, polyunsaturated) or saturated fatty acids, as well as pharmaceutically-acceptable esters, free acids, mono-, di- and triglycerides, derivatives, conjugates, precursors, salts, and mixtures thereof. In some embodiments, the fatty acid oil mixture comprises fatty acids, such as omega-3 fatty acids, in a form chosen from ethyl ester and triglyceride. In other embodiments, the fatty acids of the fatty acid oil mixture are in free acid form.

As used herein, the term "omega-3 fatty acids" includes natural and synthetic omega-3 fatty acids, as well as pharmaceutically acceptable esters, free acids, triglycerides, derivatives, conjugates (see, e.g., Zaloga et al., U.S. Patent Application Publication No. 2004/0254357, and Horrobin et al., U.S. Pat. No. 6,245,811, each hereby incorporated by reference), precursors, salts, and mixtures thereof.

The fatty acid oil mixture as disclosed herein may be derived from animal oils and/or non-animal oils. In some embodiments of the present disclosure, the fatty acid oil mixture is derived from at least one oil chosen from marine oil, algae oil, plant-based oil, and microbial oil. Marine oils include, for example, fish oil, krill oil, and lipid composition derived from fish. Plant-based oils include, for example, flaxseed oil, canola oil, mustard seed oil, and soybean oil. Microbial oils include, for example, products by Martek (now DSM). In at least one embodiment of the present disclosure, the fatty acid oil mixture is derived from a marine oil, such as a fish oil. In at least one embodiment, the marine oil is a purified fish oil.

In some embodiments of the present disclosure, the fatty acids, such as omega-3 fatty acids, of the fatty acid oil mixture are esterified, such as alkyl esters and further for example, ethyl esters. In other embodiments, the fatty acids are chosen from mono-, di-, and triglycerides.

In one embodiment, the at least one omega-3 fatty acid chosen from those defined in the Pharmacopeia Omega-3 ethyl ester 90, Omega-3 ethyl ester 60, Omega-3 triglyceride 60 and fish oil monograph.

In at least one embodiment of the delayed release capsule disclosed herein, the at least one agent comprises a fatty acid oil mixture chosen from marine oil, such as a purified fish oil, and krill oil.

In at least one embodiment, the at least one agent comprises a fatty acid oil mixture comprising from about 25% to about 100% of at least one fatty acid chosen from eicosapentaenoic acid (EPA) and docosahexaenoic acid (DHA), by weight of the fatty acid oil mixture, wherein the EPA and DHA are in a form chosen from ethyl ester, triglyceride, and free fatty acid.

In at least one embodiment, the fatty acid oil mixture comprises a higher concentration by weight of DHA than EPA. Further, the EPA and DHA are in ethyl ester or triglyceride form.

The at least one agent presently disclosed may further comprise at least one antioxidant. Examples of antioxidants suitable for the present disclosure include, but are not limited to, α-tocopherol (vitamin E), calcium disodium EDTA, alpha tocopheryl acetates, butylhydroxytoluenes (BHT), and butylhydroxyanisoles (BHA). Other examples of antioxidants include ascorbic acid and pharmaceutically acceptable salts thereof such as sodium ascorbate, pharmaceutically acceptable esters of ascorbic acid including fatty acid ester conjugates, propyl gallate, citric acid and pharmaceutically acceptable salts thereof, malic acid and pharmaceutically acceptable salts thereof, and sulfite salts such as sodium sulfite and mixtures thereof. In at least one embodiment, the at least one antioxidant comprises BHA.

In at least one embodiment, the fatty acid oil mixture comprises about 84% EPA and DHA, by weight of the fatty acid oil mixture, the EPA and DHA are in ethyl ester form, and the fatty acid oil mixture further comprises at least one other fatty acid other than EPA and DHA comprising oleic acid, and at least one surfactant comprising polysorbate 20. This composition can further comprise an antioxidant as mentioned above.

The present disclosure further relates to a delayed release capsule comprising a capsule shell comprising a combination of: gelatin chosen from type A gelatin, wherein the gelatin has a viscosity below about 4.2 mPa·sec and/or a bloom value ranging from about 60 g to about 180 g; and the gelatin is chosen from pig bone or pig skin, and alginate, in an amount of about 1% to about 10%, such as an amount of 1% to 5% by weight of the gelatin; and wherein the capsule shell encapsulates or is filled with a fatty acid oil mixture comprising from about 20% to about 100% of at least one fatty acid chosen from eicosapentaenoic acid (EPA) and/or docosahexaenoic acid (DHA), by weight of the fatty acid oil mixture, wherein the EPA and DHA are in a form chosen from ethyl ester and triglyceride; and the delayed release capsule is a soft gelatin capsule.

At Least One Surfactant

As discussed above, the at least one agent further comprises at least one suspending or solubility agent, e.g., at least one surfactant. A surfactant may, for example, lower the surface tension of a liquid or the surface tension between two liquids. For example, surfactants according to the present disclosure may lower the surface tension between a fatty acid oil mixture and an aqueous solution.

In at least one embodiment of the present disclosure, the at least one agent comprises at least one surfactant chosen from nonionic, anionic, cationic, zwitterionic surfactants, and mixtures thereof.

In at least one embodiment, the at least one surfactant comprises for example from about 0.5% to about 40%, such as from about 10% to about 30%, such as from about 10% to about 25%, by weight relative to the total weight of the at least one agent. In at least one embodiment, the at least one surfactant comprises about 20% by weight relative to the total weight of the at least one agent.

Capsule

In at least one embodiment, the delayed release capsule disclosed herein is chosen from, for example, a sustained release capsule, a controlled release capsule, and a gastroresistant capsule.

A conventional-release dosage form is an immediate-release dosage form, where the release of the API(s) is not deliberately modified and depends on the intrinsic properties of the active substance(s).

A modified-release dosage form is a preparation where the rate and/or place of release of the at least one agent is different from that of a conventional-release dosage form administered by the same route. This deliberate modification is achieved by a special formulation design and/or manufacturing method. Modified-release capsules are hard or soft capsules in which the contents, the shell, or both contain special excipients or are prepared by a special process designed to modify the rate, the place, or the time at which the at least one agent is released. Modified-release dosage forms include prolonged-release, delayed-release, and pulsatile-release dosage forms.

A "prolonged-release dosage form" is a modified-release dosage form showing a slower release of the at least one agent than that of a conventional-release dosage form administered by the same route. In a prolonged release dosage form, the drug dissolves or leaks from a matrix at a fairly constant rate and the place of release is not specified. Prolonged-release is achieved by a special formulation design and/or manufacturing method. For the purposes of this disclosure, the terms "prolonged-release dosage form," "extended-release dosage form," and "sustained-release dosage form" are equivalent.

A "pulsatile-release dosage form" is a modified-release dosage form showing sequential release of the at least one agent. Sequential release is achieved by a special formulation design and/or manufacturing method.)

A "delayed-release dosage form" is a modified-release dosage form showing a release of the active substance(s) (i.e., at least one agent) which is delayed. In a delayed release dosage form, the place or time of the release is controlled. Delayed release is achieved by a special formulation design and/or manufacturing method. Delayed-release dosage forms include gastro-resistant preparations.

A "gastro-resistant capsule" is a delayed-release capsule that is intended to resist the gastric fluid and to release the at least one agent in the intestinal fluid. Usually it is prepared by filling capsules with granules or with particles covered with a gastro-resistant coating, or in certain cases, by providing hard or soft capsules with a gastro-resistant shell.

A delayed release capsule releases the content at a later time (relative to a conventional or immediate release dosage form), while a prolonged release dosage form releases the content at a slower rate. However, combinations of both delayed release dosage forms and prolonged release dosage forms can exist.

In at least one embodiment, the delayed release capsule disclosed herein is a microcapsule. In another embodiment, the delayed release capsule is a macrocapsule.

Macro and microcapsules are particles ranging from about 20 to about 5000 microns, where the active ingredient, whether in powder form, liquid solution, or dispersion, is enveloped by a film-forming agent. Particles are finely dispersed, either by "Raleigh instability" principles or by the Wurster air suspension system before being encapsulated by the film forming agent. The particles are dried and collected from the recovery cyclone.

Microcapsules may be produced via two methods: conventional spray drying or fluidized spray drying granulation. In the first type, the material to be coated is dissolved or dispersed into a solution of water, gelatin, and alginate in a ratio of 20 to 1. The solution is atomized by turbine into a closed vessel and the particles are dried by the introduction of hot air or steam, or by flash evaporating the particles. The particles are recovered at the bottom of the cyclone. In the second type, the powder particles are suspended in the art by fluidization in a fluid bed apparatus and sprayed with a solution of the gelatin/alginate/water combination. Hot air dries the particles before they are recovered. Anticaking agent may be used in order to get a free flowing powder. A secondary spray of $CaCl_2$ may be applied to the particles.

Gelatin Formulation for Capsules

Several gelatin base formulations are available. In one non-limiting example, the target gelatin base consists of 42% gelatin, 20% glycerol, and 38% water, by weight relative to the total weight of the target gelatin base, called a "medium hard gelatin base," represents approximately 85% to 90% of all softgel products on the market. This does not exclude the use of any other gelatin base formulation. For example, the ranges of the gelatin components, relative to the total weight of the gelatin base, may range for the gelatin from about 30% to about 50%, for the plasticizers (for example, glycerol and others) from about 5% to about 35%, and water from about 20% to about 50%.

The characteristic of the target gelatin formulation, in regards to viscosity, range from approx. 3.0 Pa·sec to approx. 45.0 Pa·sec, such as, for example, a range from approx. 5 Pa·sec to approx. 30 Pa·sec. In view of the very varied number of possibilities and combinations of gelatin and alginate from different origins, using the knowledge of the art and by experimentation of the various possibilities and contrary to traditional expectations, fish gelatin, type A gelatins from different origins, type B gelatins, and mixtures thereof, together with selected alginates were found to be suitable in creating a formulation substantially similar in characteristics and viscosity to the target formulation. Those gelatins likely form a weak complex with the sodium alginate, which remained soluble at the normal pH operating values and progressively became more insoluble as the pH decreased. The degree of pH dependency was related to the type of alginate used. This process was reversible. With the further additions of small quantities of Ca, Mg, or Zn chlorides, the new gelatin formulation may become more and more insoluble at higher pHs. Additions can be accurately controlled by measuring the conductivity of the gelatin/alginate polymer solutions. With the standard gelatins used in normal capsule production, derived from skins or bones either by the alkali or the acid process, obtaining workable viscosities may be difficult. Fish gelatin is not the gelatin of choice in regular softgel manufacture as it is more difficult to process.

As the addition of the divalent ions to the gelatin/alginate polymer solution becomes more problematic with increasing concentrations, other solutions had to be found to allow intact passage of the softgel (such as, for example, SOFTLET® or UNIGEL™) from stomach into the intestinal lumen. This could be done by increasing the amount of alginate in the shell formulation or adding higher concentrations of the divalent ions. Adding them to the present formulations would have brought that particular formulation outside the production viscosity parameters. Other solutions had to be found that would not alter the production machines substantially from their present state. It was noted that when films of the target shell formulation containing the gelatin/alginate polymer were coated with solutions of calcium chloride, the Ca++ migrated very quickly into the film and rendered the films gastric insoluble. In softgel production the gelatin ribbons have to be lubricated (see FIG. 1). Lubrication is necessary to allow a seal to be made with the wedge and allow the transit of the ribbon through the heated wedge and allow sealing. The oil also serves as a mold releasing agent allowing the capsules to be cut out and separated from the main ribbon web. Traditionally this has been done by applying a controlled amount of medium chain triglycerides to both sides of the ribbon. The lubricant formulations may contain the divalent ions in the form of an emulsion or solution. The concentration of the divalent ions, and the area where it is applied, can alter the time of contact and thus the rate of migration of the divalent ions. The present medium chain triglycerides can be used to form a water-in-oil (W/O) emulsion of the dissolved cross-linking agent. This setup required the least modifications to the process, although others are also supplied as workable alternatives. The divalent ions may also be added to the capsule fill material, where they migrate into the shell during drying.

As a non-limiting example, a standard formulation for the capsules comprises:

| | |
|---|---|
| 1. Gelatin | 42% (minus the % alginate) |
| 2. Alginate | 0.2 to 20% of the gelatin |
| 3. Plasticizer (such as glycerol) | 20% |
| 4. Water | 38% or qs to 100% |
| 5. Capsule fill material | (For example, may include colorants, opacifiers, flavors) |

Methods of Making

The manufacture of softgels has been extensively reviewed (Rampurna Prasad Gullapalli, Journal of Pharmaceutical Sciences volume 99, issue 10, pages 4107-4148, October 2010). The present disclosure is further directed to a method of manufacturing a delayed release capsule comprising a capsule shell comprising a combination of gelatin chosen from type A gelatin, or a combination of type A and type B gelatin, wherein the gelatin has a viscosity below about 4.2 mPa·sec and/or a bloom value below about 290 g; and alginate, in an amount ranging from about 0.2% to about 20%, by weight of the gelatin, wherein the alginate has a viscosity ranging from about 2 mPa·sec to about 600 mPa·sec. As described, the viscosity of the alginate does not range from about 45 mPa·sec to about 420 mPa·sec when the alginate is a high G alginate; wherein the capsule shell encapsulates at least one agent, and the delayed release capsule is a soft capsule, a film-enrobed unitary core product (e.g., a SOFTLET®), or a soft capsule comprising a soft shell encapsulating a solid unit dosage form or multiple solid dosage forms in the form of beadlets or granules (e.g., a UNIGEL™ capsule).

In an embodiment, the delayed release capsule comprises a type A gelatin having a viscosity below 4.2 mPa·sec and/or a bloom value ranging from 60 g to 180 g, and comprises at least one of pig bone and pig skin. The alginate, which comprises a high M alginate having a viscosity of 520 mPa·sec., is present in an amount of 1% to 5% by weight of the gelatin. In this embodiment, the delayed release capsule is a soft capsule, and the soft capsule shell encapsulates:

at least one fatty acid oil mixture comprising from 30% to 100% of at least one fatty acid chosen from eicosapentaenoic acid (EPA) and/or docosahexaenoic acid (DHA), by weight of the fatty acid oil mixture, wherein the EPA and DHA are in a form chosen from ethyl ester and triglyceride;

at least one vitamin, mineral, or both, fatty acid oil mixture of plant, animal or microbial, a probiotic product, either plant or microbial;

at least one film-enrobed unitary core product or multiple solid dosage forms in the form of beadlets or granules.

Figure 3:
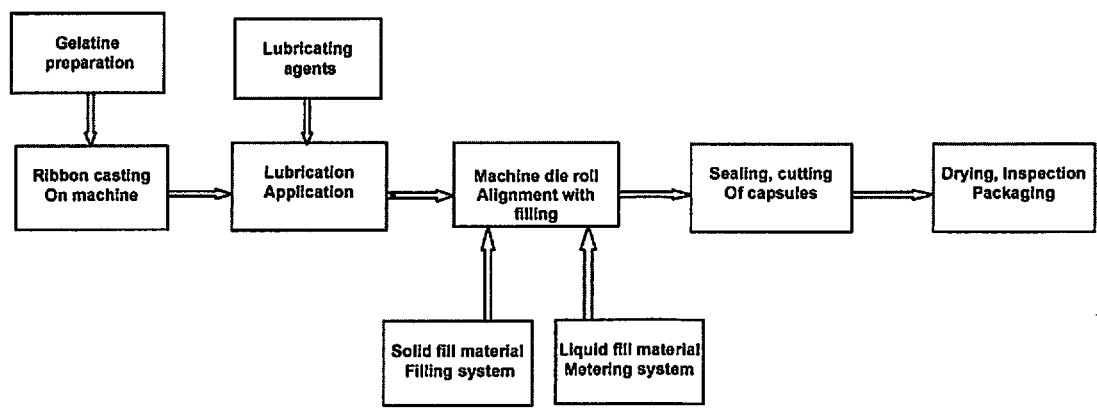
FIG. 3 shows an example production line of alginate-gelatin capsules.

FIG. 3 schematically depicts a production line for softgel capsules as described above. The gelatin/alginate/plasticizer/water mixture is prepared and brought to the machine. With the help of two casting boxes, two uniform thickness ribbons are formed and lubricated on both sides. The product feed mechanisms for liquid or solids, acting either independently or in conjunction with each other, are synchronized with the dies, and the cavities formed by the dies are filled with the metered ingredients. The rotation of the dies, heat, pressure seal and cut the capsules. The capsules are then dried, inspected, and packaged.

The present disclosure is further directed to a method of manufacturing a delayed release capsule comprising a capsule shell comprising a combination of: gelatin chosen from type A gelatin, or a combination of type A gelatin and type B gelatin, wherein the gelatin has a viscosity below about 4.2 mPa·sec and/or a bloom value below about 290 g; and alginate, in an amount ranging from about 0.2% to about 20%, by weight of the gelatin; wherein the delayed release capsule is a hard capsule, comprising the steps of:

(a) preparing a mixture of the gelatin and the alginate;

(b) pouring the mixture into a heated dipping dish, equipped with an internal pump, of a standard hard gelatin capsule production machine to form a film of the mixture;

(c) producing a body and cap part of the capsule on both sides of the machine, wherein two sizes of molding pins are used, a lubricant is applied to the pins in the grease section of the machine, the greased pins are dipped in the gelatin mixture of the dipping dish, rotated and brought to the upper deck of the machine, and cooled down, while dry air is continuously passed over the coated pins, and the film is stripped from the pins, trimmed to the exact size to form a body and cap of the film;

(d) joining the body and cap part in joining blocks to form a capsule; and (e) ejecting the capsule onto a conveyor belt for further processing.

Softgel, SOFTLETS®, and UNIGEL™ Production Process

For the shell component of the capsule, in essence, the gelatin solution is made by dissolving the gelatin, the plasticizers, glycerol, sorbitol or others in water and heating the mixture under vacuum and temperature of 60 to 80° C. until a clear solution, free of air, is obtained. The gelatin base is then collected, adjusted for pH and stored in heated tanks until such time it can be used. Other materials such as flavors, colors, opacifiers can be added at that stage. The ratio gelatin to plasticizer can be changed to make the shell either harder or softer.

For the content of the capsules, the active ingredients (i.e., the at least one agent) are mixed, dissolved or suspended according to the recipe or batch control documents into oily or polyethylene glycol based carriers. This solution or suspension is de-aired and kept under nitrogen cover until the time of use.

The manufacturing process is shown in FIG. 1.

The gelatin base flows from the gelatin tank into a spreader box. This standard device casts a ribbon of known thickness on both sides of the machine on two cooled drums, which set the gelatin into a flexible film. The ribbon is peeled off from the drum and passes through two lubricating, e.g. oil rollers. Those rollers apply a film of lubricant on both sides of the ribbon. The ribbon is rolled over between the die rollers and the wedge. The die rollers have pockets cut into their surface in the shape of the desired shape and size of the capsules. The capsule fill material flows through a product pump, which meters the quantity of liquid, suspension or solution through holes in the wedge. The pressure of the pumps expands the ribbon into the pockets of the dies. The wedge is heated to a temperature just above the melting point of the gelatin. The heat supplied by the wedge and the rotation of the die rollers seals the content of the capsule between both ribbons. Further rotation of the die rollers, under pressure, cut out the capsules from the ribbon. The capsules are collected and transferred to a rotating air dryer, where they lose approx. 30% of their moisture. The capsules are then transferred onto trays and placed in an air dryer where continuously dry air is passed over the surface of the capsules. Drying takes 2 to 7 days depending on the composition of the shell. Capsules are then inspected and packed.

In the case of the production of SOFTLETS®, the pump assembly is replaced by a dry feeding mechanism synchronized with the rotation of the die rollers. The tablet is guided through the wedge and placed between the two ribbons of gelatin into the pockets of the die rollers. The rotation of the dies and the heat supplied by the wedge seals the gelatin around the tablet. The process is then completed as described above.

In the case of the production of UNIGEL™ softgel capsules, two secondary die rollers are placed on top of both gelatin ribbons, in front of the wedge, and pockets are formed in the gelatin ribbon by applying a vacuum to the film. Two synchronized feeding systems feed the tablet, capsule, or granules in the pockets so formed. When the two pockets on each side are aligned with the wedge injection holes, the standard liquid pump system injects a measured amount of liquid into the two halves, filling the interspace between the solid particles and the shell membrane. The rotation, the heat supplied by the wedge, and the pressure on the die rollers seal and cut out the capsules (see, e.g., International Patent Application Publication No. WO2012/017326). The process is then completed as described above.

The present disclosure modifies the standards production process in several new ways in order to introduce, where appropriate, at least one cross-linking agent, such as $CaCl_2$ and/or other divalent ions, into the gelatin/alginate solution, by application through the lubricating system or by way of the capsule fill material.

With reference to FIG. 1, in at least one embodiment, the capsule is a soft gelatin capsule, and the capsule fill material is added through a positive displacement pump placed above the wedge (4), and subsequently through holes in the wedge (4).

In at least one embodiment, the capsule is a film-enrobed unitary core product, and the capsule fill material is added through a dry feeding mechanism synchronized with the rotation of the die rollers, and subsequently through holes in the wedge (4).

In at least one embodiment, the alginate is present in an amount ranging from about 0.2% to about 5%, by weight of the gelatin or in an amount ranging from about 5% to about 15%, by weight of the gelatin.

In at least one embodiment, the capsule fill content of the at least one agent ranges from about 0.150 g to about 1.300 g, such as from about 0.600 g to about 1.200 g, such as from about 0.800 g to about 1.000 g.

Production of SOFTLETS®

As mentioned above, SOFTLETS® are tablets that are enrobed with a coat of gelatin using the same softgel production machine, where the medicine pumping assembly has been modified to inject single tablets between the two ribbons at point 4 (see FIG. 1). The above method of application of the $CaCl_2$ to the gelatin, by way of the lubricating system, can now be applied to the production of SOFTLETS®. This method of encapsulation has been described in U.S. Pat. No. 6,482,516.

Production of Hard Gelatin Capsules

The gelatin used in the manufacture of hard gelatin capsules is of a different composition than the gelatin that is used for the production of softgels. The gelatin is usually a type A or type B gelatin of bone or hide origin, manufactured according to the acid or the lime process. Mixtures of both types may be used. The gelatin as disclosed herein, has a bloom value that ranges from about 150 to about 290 g and a viscosity that ranges from about 2.5 to about 5.0 mPa·sec. In at least one example, bloom ranges from about 180 to about 290 g and viscosity ranges from about 2.8 to about 4.5 mPa·sec.

In the standard production process, a solution in water is made of gelatin ranging from about 25 to about 40%, relative to the weight of the solution. The gelatin is mixed with water and the mixture is heated at a range from 60 to 70° C., for example under vacuum, until all the gelatin is dissolved and a clear solution is obtained. The viscosity may be measured as a control. At that stage other ingredients, such as opacifiers and dyes, can be added. The gelatin solution is split into 2 tanks, one destined for the body part of the telescoping capsule and the other to produce the cap. Both can be of different colors to help to identify the final product. The solution is kept at constant temperature until such time it is required for use in the capsule production machine.

The production of the hard gelatin capsules and the filling thereof has been described in the cited publication. (Fridrun, Podczeck, *Pharmaceutical capsules*, Pharmaceutical press, 2004). The gelatin is poured into the heated dipping dish, equipped with an internal pump, maintaining the liquid level at a constant height. The hard gelatin capsule production machine produces the body and the cap part of the capsules on both sides of the machine, the process being symmetrical. Two sizes of molding pins are used, one size on the left of the machine forming the body of the capsule, the other on right hand side of the machine forming the caps. The body pins are slightly smaller in diameter then the cap, allowing the body of the capsule to slide into the cap at the end of the production process.

Figure 2:
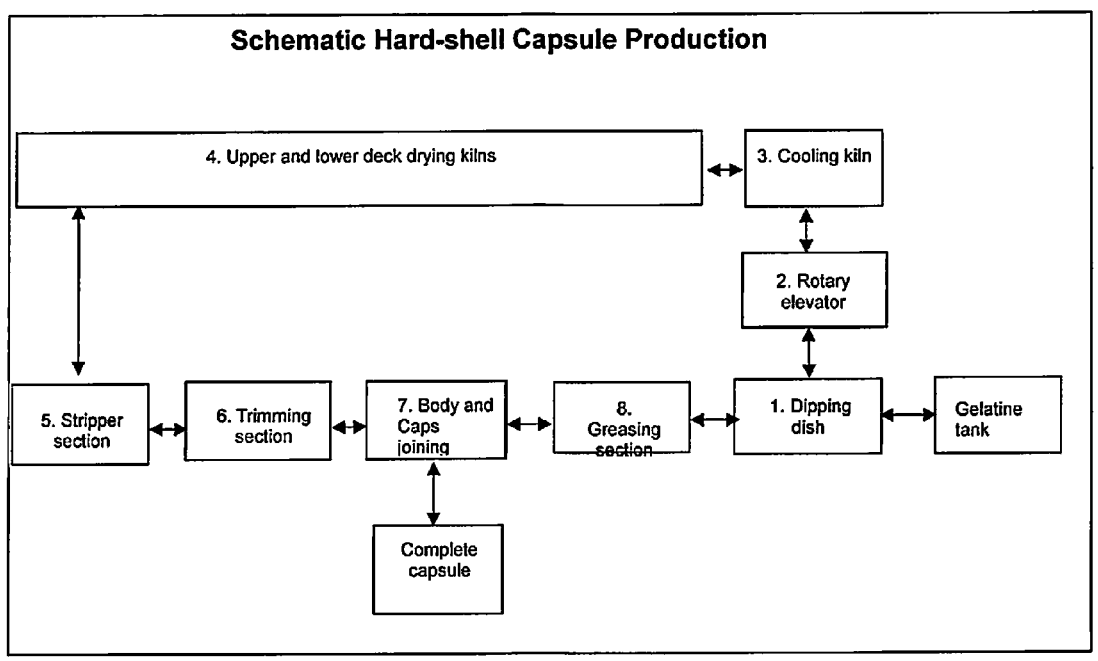
FIG. 2 is a schematic depiction of the manufacturing process of hard gelatin capsules.

In the present disclosure the composition of the gelatin solution is modified. Part of the gelatin is replaced with sodium alginate ranging from about 1 to about 20%, such as from about 2 to about 15%. The quantity of sodium alginate added will depend on the final viscosity requirements of the production process and the viscosity and origin of the sodium alginate. (FIG. 2, ref. gelatin).

The gelatin film on the molding pins would be very difficult to remove from the pins without a pin lubricant. A lubricant is applied to the pins in the grease section of the machine once the body and the caps have been stripped from their film. (FIG. 2. Ref 1). This food type grease is formed by saponifying a non oxidizing saturated vegetable oil, such as cotton seed oil or arachis oil with calcium hydroxide or calcium oxide, at high temperatures and for example in a pressurized vessel. Optionally, beeswax is added to the lubricant formulation. On cooling down, a lubricating oil is added such as a pharmaceutical grade low viscosity paraffin or a medium chain triglyceride or other pharmaceutical acceptable oils. The mixture is allowed to cool down under controlled conditions.

In at least one embodiment, a saturated solution of $CaCl_2$ is emulsified into the lubricant.

In at least one embodiment, the capsule fill volume of the at least one agent ranges from about 0.200 $cm^3$ to about 1.300 $cm^3$, such as from about 0.600 $cm^3$ to about 1.200 $cm^3$, such as from about 0.800 $cm^3$ to about 1.000 $cm^3$.

Alginate-Gelatin Compositions

In addition to the delayed release capsules disclosed herein, the present disclosure is also directed to an alginate-gelatin film/matrix for making a delayed release capsule comprising a capsule shell comprising a combination of: gelatin chosen from type A gelatin, or a combination of gelatin type A and type B gelatin, wherein the gelatin has a viscosity below about 4.2 mPa·sec and/or a bloom value below about 290 g; and alginate, in an amount ranging from about 0.2% to about 20%, by weight of the gelatin, wherein the alginate has a viscosity ranging from about 2 mPa·sec to about 600 mPa·sec; wherein the capsule shell encapsulates or is filled with at least one agent; and the delayed release capsule is chosen from a soft capsule and a hard capsule; with the provisos that the viscosity of the alginate is not from about 45 mPa·sec to about 420 mPa·sec when the alginate is a high G alginate.

The following examples are intended to illustrate the present disclosure without, however, being limiting in nature. It is understood that the skilled artisan will envision additional embodiments consistent with the disclosure provided herein.

EXAMPLES

Example of Lubricating Grease

Typical formulation of a standard lubricating grease:

| | |
|---|---|
| Cotton Seed Oil | 2.00 kg |
| CaO (Calcium Oxide) | 0.27 kg |
| Water | 0.05 kg |
| Beeswax (optionally) | 0.20 kg |
| Medium Chain Triglycerides | 2.00 kg |

Modified Lubricating Grease

The oil and the CaO were heated in a pressure vessel until it reached 95° C., then the water was added. The pressure vessel was closed and heated to 130° C. The reaction started and the temperature increased. The heat source was withdrawn and the reaction allowed to complete. The resulting mixture was cooled down and the pressure released. When the mixture reached approx. 90° C., 0.2 kg of a saturated solution of $CaCl_2$ was added and dissolved. The medium chain triglycerides were then added. The resulting grease mixture was mixed well and cooled down to room temperature. Crystal size and signs of bleeding were examined.

The grease was applied to felt pads or other porous materials and inserted into the grease cartridges (see FIG. 3). The cartridges were mounted onto a sliding table that moved in and out, synchronized with the movement of the bars and pins. The forwards-moving sliding table moved the rotating cartridges over the pins to apply a film of grease. In this disclosure the composition of the grease was changed and a saturated solution of CaCl$_2$ was emulsified into grease. The CaCl$_2$ migrated into the wet gelatin/alginate mixture and cross-linked the alginate part of the body and cap part of the capsule.

The greased pins are then dipped in the gelatin/alginate mixture of the dipping dish (FIG. 2, ref. 2), rotated (FIG. 2, ref. 3) and brought to the upper deck of the machine. The molds (pins) coated with gelatin/alginate are cooled down to set the gelatin/alginate in the cooling kiln (FIG. 2, ref. 3). The pins are then moved along the upper deck, down the lower deck, while dry air is continuously passed over the coated pins (FIG. 2, ref. 4). The gelatin/alginate films are then stripped from the pins, (FIG. 2, ref. 5), trimmed to the exact size (FIG. 2, ref. 6) and both body and caps are joined in the joining blocks (FIG. 2, ref. 7) and ejected onto a conveyor belt for further processing an inspection and packaging.

Examples of Gelatin/Alginate Films

Films of gelatin/alginate were prepared and examined for disintegration in acid simulated gastric liquid (SGF) and subsequently in simulated intestinal fluid (SIF).

The alginate was first dispersed into the required quantity of water according to the standard gelatin formulation (described below), in the desired amount. The alginate dispersion was heated at 60 to 70° C. until a clear solution, free of particles was obtained. The solution was allowed to cool down. The glycerol was then added to the alginate solution followed by the gelatin. The mixture was allowed to stand until all the free water and glycerol were absorbed by the gelatin. The mixture was then heated to 60 to 70° C., until a clear solution, free of air, was obtained. The solutions were measured for viscosity using a Brookfield viscometer, and the results evaluated against the standard gelatin. Films with a uniform thickness of 1 mm were cast with a film-casting tool on a flat cooled surface to allow the gelatin/alginate mixture to set. All films were divided into three parts. No CaCl$_2$ was applied to the first part, a 20% CaCl$_2$ solution was applied to the second part, and a 40% CaCl$_2$ solution was applied to the third part. In each case, the respective CaCl$_2$ solution was applied to the top surface of the films and removed with a laboratory paper cloth after 45 sec. The films were removed and first air-dried. The films were then placed in a closed sealed cabinet. Dehydrated CaCl$_2$ crystals were placed in the cabinet. The final relative humidity (RH) obtained in the cabinet was 20 to 25%. The films remained in the cabinet until firm and a constant RH was obtained. The drying time was approx. 7 days.

Parts of the film were tested with a Texture Analyser and the Young's modulus and Breaking Strength calculated.

A proprietary validated Simulated Gastric Fluid (SGF) was prepared containing the following ingredients: bile extract, lecithin, pepsin, sodium chloride and water. This solution was adjusted to a pH of 1.6.

The films were cut into similar rectangular shaped pieces and placed in the above Simulated Gastric Fluid (SGF) being maintained at a temperature of 37° C. (Where capsules were used, those were directly transferred into the SGF and monitored for disintegration.) The disintegration status of the strips was observed every 2 minutes. The films first absorbed water and increased in thickness. This is a normal occurrence with gelatin films. No Ca-treated sample disintegrated or dissolved within the 2.0 hours resident time. The disintegration time of samples not treated with Ca was dependent on the concentration of the alginate used in the film, indicating that one does not always need the CaCl$_2$-treatment to protect the films against disintegration and that 2 modes of action were taking place according to the type of gelatin and Sodium Alginate being used.

The films were then transferred into a proprietary validated Simulated Intestinal Fluid (SIF), by combining one part of the SGF with 4 parts of a solution of the following ingredients: bile extract, lecithin, trizma maleate, sodium chloride and water, and adjusted to a pH of 6.6. The films were monitored for disintegration by recording the disintegration time of the films or the capsules.

The following gelatin and sodium alginates were used to establish relationships and characteristics of interaction of Gelatin and Alginate and Calcium Chloride:

| Bovine (standard) gelatin (BL) | Type B | 159 g bloom | Viscosity 23 to 42 mP |
|---|---|---|---|
| Acid pig bone gelatin (AL) | Type A | 150 g bloom | Viscosity 23 to 42 mP |
| Acid bovine bone Gelatin (AH) | Type A | 205 g bloom | Viscosity 23 to 42 mP |
| Fish skin Gelatin (FL) | Type A | 139 g bloom | Viscosity 18 to 40 mP |
| Fish skin Gelatin (FH) | Type A | 270 g Bloom | Viscosity 18 to 40 mP |
| Sodium Alginate (ML) | | | Viscosity 5 to 50 mPa · sec |
| Sodium Alginate (Mm) | | | Viscosity 520 mPa · sec |
| Sodium Alginate (GL) | | | Viscosity 5 to 20 mPa · sec |
| Sodium Alginate (Gm) | | | Viscosity 340 mPa · sec |

The following standard gelatin formulation was used as a starting point:

| Gelatin | 42% |
|---|---|
| Glycerol | 20% |
| Water | 38% |

Additional Examples of Gelatin and Alginate

The bovine hide gelatin (BL) is the most frequently used gelatin in the current, standard softgel encapsulation process.

Four different sodium alginates were used for preparation of solutions and films. Table 1 presents the four alginates with corresponding product information (source of origin, quality, description, and abbreviation).

TABLE 1

Product information and abbreviations for the different sodium alginates applied for preparation of solutions and films.

| Origin | Quality | Description | Abbreviation* |
|---|---|---|---|
| L. digitata | Pharma grade | High M, low viscous | ML |
| L. digitata | Food grade | High M, medium viscous | Mm |
| L. hyperborea | Pharma grade | High G, low viscous | GL |
| L. hyperborea | Food grade | High G, medium viscous | Gm |

*The medium viscous alginates are abbreviated to Mm and Gm with a lower case "m" for "medium", to avoid confusion with the abbreviation for mannuronic acid (M).

Example of Alginate-Gelatin Viscosity Synergistic Effect
Experimental Results

The introduction of alginate into the gelatin base contributed to an increase in viscosity. The viscosities of the systems containing both gelatin and alginate were all higher than the sum of the individual gelatin and alginate solutions measured separately at similar conditions.

The plausible synergistic effect between gelatin and alginate can further be illustrated by a calculated interaction parameter. The interaction parameter is the ratio of the viscosity of the combination to the sum of the viscosities of the gelatin and alginate systems measured separately.

The samples in Table 2 were prepared with 42% w/w water, 38.5% w/w gelatin, 18.71% w/w glycerol and 0.79% w/w and sodium alginate (2% of the gelatin weight was replaced with sodium alginate). The viscosity was measured with a Brookfield viscometer at 60° C., 60 rpm, spindle 64, and a measuring time of 1 minute.

TABLE 2

Viscosity of individually measured solutions and the calculated combination, and the interaction parameter.

| System | $\eta_{gelatin}$ (measured) | $\eta_{alginate}$ (measured) | $\eta_{alginate} + \eta_{gelatin}$ (calculated) | $\eta_{gelatin + alginate}$ (measured) | Interaction parpameter |
|---|---|---|---|---|---|
| FL, 2% ML | 1098 | 35.9 | 1134 | 4290 | 3.8 |
| FL, 2% Mm | 1098 | 560 | 1658 | 7380 | 4.5 |
| FL, 2% GL | 1098 | 9.3 | 1107 | 1691 | 1.5 |
| FL, 2% Gm | 1098 | 450 | 1548 | 7980 | 5.2 |
| FH, 2% ML | 2976 | 35.9 | 3012 | 6620 | 2.2 |
| FH, 2% GL | 2976 | 9.3 | 2985 | 3730 | 1.2 |
| AL, 2% ML | 1609 | 35.9 | 1645 | 5584 | 3.4 |
| AL, 2% GL | 1609 | 9.3 | 1618 | 2195 | 1.5 |
| AH, 2% ML | 2375 | 35.9 | 2411 | 8260 | 3.4 |
| AH, 2% GL | 2375 | 9.3 | 2384 | 3110 | 1.3 |
| BL, 2% GL | 5500 | 9.3 | 5509 | 9540 | 1.7 |

A synergistic effect between gelatin and alginate was observed from the viscosity tests. The synergy is dependent on the type of gelatin and alginate used.

Dissolution Test of Softgel Formulations

In the preparation of films and capsules, it was desired to use gelatin/alginate solutions where the viscosity was within reasonable working limits. Based on this viscosity selection criteria several selected combinations of gelatin/alginate were tested in simulated gastric and intestinal fluid. Table 3 gives an overview of the dissolution results for different softgel formulations made from gelatin and alginate.

TABLE 3

Dissolution results for different softgel combinations with and without Ca-treatment.

| Gelatin Type | Alginate Type | Alginate conc. % | Viscosity mPa · sec | SGF min | SIF min (no CaCl$_2$) | SIF min (CaCl$_2$ 20%) | SIF min (CaCl$_2$ 40%) |
|---|---|---|---|---|---|---|---|
| AH | GL | 4 | 11140 | Failed | 0 | 16 | 24 |
| FH | GL | 2 | 7866 | Failed | 0 | 10 | 12 |
| FL | Gm | 2 | 18065 | 120 | 26 | 12 | 14 |
| AL | ML | 3 | 15250 | 120 | 16 | 8 | 12 |
| FH | ML | 2 | 14740 | Failed | 0 | 8 | 10 |
| FL | ML | 2 | 9170 | 120 | 12 | 8 | 8 |
| FL | ML | 3 | 12269 | 120 | 22 | 8 | 12 |
| AL | Mm | 1 | 16152 | 120 | 18 | 8 | 6 |
| FH | Mm | 1 | 12820 | Failed | 0 | 4 | 8 |
| FL | Mm | 2 | 16589 | 120 | 22 | 8 | 10 |
| BL | ML | 2 | 34974 | | — | — | |

Interpretation of the Results:

1. The standard BL gelatin on its own was difficult to use as the viscosity exceeded by far the working limits. Use of type B gelatin as the sole gelatin was therefore excluded.

2. There are 2 suggested modes of gelatin/alginate interaction:
   ML/Mm where it is clearly shown that CaCl$_2$ coating is not required in order to achieve resistance to SGF
   GL/Gm where CaCl$_2$ is generally required to achieve resistance to SGF, and further that their action is dependent on the concentration.

The interaction of the gelatin with the alginate is also dependent on the molecular weight and/or the type of gelatin.

The dissolution time is related to the degree of interaction between gelatin and alginate: a stronger interaction (higher interaction parameter) is followed by an increased dissolution time.

TABLE 4

Coherence between synergistic effect/interaction between gelatin and alginate, and dissolution time in simulated intestinal fluid (SIF)

| System | Interaction parameter | Dissolution time in SIF (min) |
|---|---|---|
| FH-2% GL | 1.2 | Failed |
| FH-2% ML | 2.2 | Failed |
| FL-2% ML | 3.8 | 12 |
| FL-2% Mm | 4.5 | 22 |
| FL-2% Gm | 5.2 | 26 |

Production Test

In order to demonstrate that the results could be reproduced in a production situation using the standard rotary die encapsulation equipment, a test was set up using, from a production standpoint, the worst case formulation: FL-2% Mm. The batch size was approximately 220 kg. Good quality, sparkling clear capsules were produced during a 2 hour production run. After drying, the capsules were tested with a disintegration test, and showed clearly that the capsule shell would withstand 2 hours of SGF, thereby demonstrating that a capsule which does not disintegrate in SGF for 2 hours could be successfully made. Stability of the capsules was evaluated at the time of manufacture and after 1 month storage at 40° C. and 75% relative humidity (RH).

A second test applying a calcium chloride solution, in this case a 27% solution, in position 4 on the machine, showed similar disintegration results as obtained with the films.

The disintegration experiments were conducted in Simulated Gastric Fluid (SGF) containing pepsin, bile extract, lecithin and NaCl. The capsules were put into the medium and the disintegration time was noted when the first bubble of API leaked out of the capsule. The trial capsules were tested right after production, at the start of the stability test, and after 1 month at 40° C. and 75% RH. Immediately after production, it was noted that API leaked out from the seam after 2 minutes, but the capsule shell was not dissolved. At the start of the stability test, it was observed that the API had leaked out after approximately 2 minutes, most likely from the seam. After 1 month at 40° C. and 75% RH, it was observed that the capsule preserved the total content of API for more than 2 hours in SGF (disintegration time>2 hours).

TABLE 5

Stability Results from 1 month at 40° C. and 75% relative humidity.

Preliminary Results - Start Stability

|  | Test 1 (No CaCl$_2$) | Test 2 (Cross-linked with CaCl$_2$) |
| --- | --- | --- |
| Appearance | CO | CO |
| Odor | CO | CO |
| Hardness (N) | 11 | 11 |
| Shell water content (W %) | 5.2 | 6 |
| Anisidine value (—) | 8 | 8 |
| Peroxide value (meq/kg) | 3.6 | 3.8 |
| EPA (mg/g) | 304 | — |
| DHA (mg/g) | 221 | — |
| EPA & DHA (mg/g) | 525 | — |
| Total n-3% | 60.6 | — |
| Glycerol (mg/g) | 409 | 409 |

Preliminary Results - 1 Month Stability

|  | Test 1 |
| --- | --- |
| Appearance | NC |
| Odor | NC |
| Disintegration (hours) | >2 h |
| Anisidine value (—) | 9 |
| Peroxide value (meq/kg) | 0.3 |

CO = "conform"
NC = "not conform"

The above stability results show for instance that oxidation parameters such as anisidine value and peroxide value did not increase significantly during 1 month storage at 40° C. and 75% RH.

Example of Delayed Release Capsule Containing at Least One Agent

The following formulation was used to make transparent capsules filled with 1000 mg of clear light yellowish oil of approximately 65% omega-3 acid ethyl esters. The capsules were oblong size 20.

TABLE 6

Capsule formulation (FL2% Mm) used in the production test.

| Purified water | 38.00% | 83.60 kg |
| --- | --- | --- |
| Glycerol | 20.00% | 44.00 kg |
| High M, medium viscous Na-alginate (Mm) | 0.84% | 1.85 kg |
| Low bloom, acid processed fish gelatin (FL) | 41.16% | 90.55 kg |

Active Pharmaceutical Ingredient (API)

The active drug substance was 65% ethyl esters (EE) comprising (approximately):

| EPA EE | 330 mg/capsule |
| --- | --- |
| DHA EE | 220 mg/capsule |
| Total omega-3 acid (EE) | ~65% (w/w) |

Softgel Formulations with Type A Gelatin and High M Alginate—not Treated with Cross-Linking Ions Since the production test with type A fish gelatin (Table 6) resulted in capsules from which the content rapidly leaked out after 2 h in SGF, additional experiments were performed with an equivalent gelatin from mammalian origin.

Test 1
Formulation Composition

TABLE 7

Composition of solutions with 60% w/w water and 2, 4 and 6% of the gelatin weight replaced by alginate.

| Component | 2% alginate (% w/w) | 4% alginate | 6% alginate |
| --- | --- | --- | --- |
| Gelatin | 26.55 | 26.01 | 25.47 |
| Alginate | 0.54 | 1.08 | 1.63 |
| Glycerol | 12.90 | 12.90 | 12.90 |
| Water | 60.00 | 60.00 | 60.00 |
| Total | 100.00 | 100.00 | 100.00 |

Sample Preparation

Samples were prepared with 60% w/w water in the formulation. Alginate was dissolved in water under vigorous stirring until a homogenous solution was obtained. The glycerol was then added followed by further mixing. Gelatin was added and the mixture was left to stand for 5-10 minutes to allow for complete hydration of the gelatin powder. The mixture was then melted overnight at 60° C. The following day, thin gelatin/alginate gels were cast, with a uniform thickness of 1 mm, a thickness corresponding to the standard ribbon thickness in the conventional softgel process. The gelatin/alginate samples were placed in a drying box equipped with an electrical fan and molecular sieves. After drying, rectangular test samples were cut out and weighed.

Dissolution Test

A dissolution test in simulated gastric fluid (SGF) containing bile extract, lecithin, sodium chloride and pepsin was performed. The gelatin/alginate samples were placed in SGF at 37° C. for 120 minutes without stirring. Gastro-resistance was evaluated with visual inspection of the different test samples.

Results

The formulations with 60% w/w water formed nice, clear, air-free solutions with acceptable viscosities. The elasticity was not optimal due to a lower amount of gelling agent. Table 8 shows the results from the dissolution test.

TABLE 8

Dissolution results for samples made from 60% w/w water solutions and 2, 4 and 6% gelatin weight replaced with alginate. The water content was not measured on these samples. The gels were difficult to dry to an acceptable moisture level. Most probably the moisture content was high in these gels since they were very soft and pliable prior to analysis.

| Sample | Weight (g) | Thickness (mm) | SGF |
| --- | --- | --- | --- |
| AL-2% Mm-1 | 0.51 | 0.46 | Fractured before 120 min |
| AL-2% Mm-2 | 0.51 | 0.46 | Fractured before 120 min |
| AL-4% Mm-1 | 0.50 | 0.44 | Very fragile |

TABLE 8-continued

Dissolution results for samples made from 60% w/w water solutions and 2, 4 and 6% gelatin weight replaced with alginate. The water content was not measured on these samples. The gels were difficult to dry to an acceptable moisture level. Most probably the moisture content was high in these gels since they were very soft and pliable prior to analysis.

| Sample | Weight (g) | Thickness (mm) | SGF |
| --- | --- | --- | --- |
| AL-4% Mm-2 | 0.50 | 0.45 | Very fragile |
| AL-6% Mm-1 | 0.49 | 0.42 | Resistant to SGF for 120 min. Much stronger than the 2 and 4% samples. |
| AL-6% Mm-2 | 0.52 | 0.52 | Resistant to SGF for 120 min. Much stronger than the 2 and 4% samples. |

Test 2
Formulation Composition

TABLE 9

Composition of solutions with 42% w/w water and 3, 4 and 5% by weight of gelatin weight replaced by alginate.

| Component | 3% alginate | 4% alginate (% w/w) | 5% alginate |
| --- | --- | --- | --- |
| Gelatin | 38.11 | 37.72 | 37.33 |
| Alginate | 1.18 | 1.57 | 1.96 |
| Glycerol | 18.71 | 18.71 | 18.71 |
| Water | 42.00 | 42.00 | 42.00 |
| Total | 100.00 | 100.00 | 100.00 |

Sample Preparation

Samples were prepared with 42% w/w water in the formulation. Alginate was dissolved in water under vigorous stirring until a homogenous solution was obtained. The glycerol was then added followed by further mixing. Gelatin was added and the mixture was left to stand for 5-10 minutes to allow for complete hydration of the gelatin powder. The mixture was then melted overnight at 60° C. The following day, thin gelatin/alginate gels were cast, with a uniform thickness of 1 mm, a thickness corresponding to the standard ribbon thickness in the conventional softgel process. The gelatin/alginate samples were placed in a drying box equipped with an electrical fan and molecular sieves.

Dissolution Test

Rectangular test samples were cut out and weighed.

A dissolution test in simulated gastric fluid (SGF) containing bile extract, lecithin, sodium chloride and pepsin was performed. The gelatin/alginate samples were placed in SGF at 37° C. for 120 minutes without stirring. Gastro-resistance were evaluated with visual inspection of the different test samples.

Water Content

The water content in the dried gelatin/alginate samples was determined by semi-automated Karl Fisher (KF) titration. During this procedure, the sample was heated to 150° C. and nitrogen gas carried the evaporating water to the titration device. Rectangular test samples were cut out and weighed, and the water content in the samples was calculated based on the original weight and the weight of evaporated water.

Results

Samples prepared with 42% w/w water in the formulation. Thick, viscous solutions with a significant amount of air bubbles were formed. The gels became grainy after casting, but the elasticity was optimal. KF titration showed that the water content of the samples from Test 2 was approximately 8%. Table 10 provides the results from the dissolution test in SGF.

TABLE 10

Dissolution results for samples made from 42% w/w water solutions and 3, 4 and 5% gelatin weight replaced with alginate.

| Sample | Weight (g) | Thickness (mm) | SGF |
| --- | --- | --- | --- |
| AL-3% Mm-1 | 0.46 | 0.75 | Fragile, fractured before 120 min |
| AL-3% Mm-2 | 0.43 | 0.75 | Fragile, fractured before 120 min |
| AL-4% Mm-1 | 0.46 | 0.89 | Fragile, but did not fracture within 120 min |
| AL-4% Mm-2 | 0.48 | 0.89 | Fragile, but did not fracture within 120 min |
| AL-5% Mm-1 | 0.52 | 0.88 | Resistant to SGF for 120 min |
| AL-5% Mm-2 | 0.50 | 0.88 | Resistant to SGF for 120 min |

KF titration demonstrated that the water content in the samples in Test 3 was approximately 5%.

CONCLUSIONS

Gastro-resistant samples can be produced from a combination of type A pig bone gelatin and high M, medium viscous alginate. The resistance to gastric fluid improved when alginate concentration increased. However, viscosity also increased along with alginate concentration, which results in a solution which is "difficult" to handle.

Resistance to simulated gastric fluid seemed to be related to the moisture content. A comparison between Test 2 and Test 3 showed that the same type of gels exhibited improved gastro-resistance after one additional day of drying.

On the basis of these results, the preferred formulation of this combination of gelatin and alginate should contain an amount of alginate which represents approximately 4-5% replacement of the gelatin weight. Furthermore, the drying of the gels must be adequate. The moisture content should be below 8%.

Viscosity issues may be overcome if the formulation is diluted with water. However, 60% w/w water was too much since the elasticity was weakened due to a lower amount of gelling agent. The water content should preferably be below 50% to ensure that an adequate elasticity is preserved during production of the softgels.

Example of Delayed Release Hard Shell Capsule

A mixture was made consisting of:

| Fish gelatin (FL) | 30% |
| --- | --- |
| Alginate (Mm) | 1.5% (or 5% of the gelatin weight) |
| Water | 68.5% |

The alginate was dissolved in the water at around 60° C. The solution was left to cool and the gelatin was added. The mixture was left to stand until all water was absorbed by the gelatin and then heated to 60° C. until fully dissolved and free of air.

Size 1 and 0 hard gelatin capsule mold pins of body and cap were used to hand dip the pins in the gelatin mixture and left to stand to dry for 3 to 4 hours. After the drying period the gelatin shell could not be removed from the pins.

A grease according to the example lubricating grease disclosed above was used to lubricate the pins, and the process was repeated. The pins were dried for 3 to 4 hours at room temperature and 30% relative humidity (RH). Tools were made having holes with a slightly higher diameter then the pins molds. It was then possible to strip the gelatin shells from the pins, cut them to the required length, and join body and cap together.

The shells were then tested in HCl 0.1 N at 37° C. and found to resist the SGF for 2 hours. A SIF solution, based on "Biorelevant Dissolution Media Simulating the Proxial Human Intestinal Tract" by E. Jantratid and J. Dressman, composed of sodium chloride, sodium bicarbonate, citric acid, and a surfactant was used to test the dissolution.

Another alginate-gelatin combination was made consisting of a 3% Mm alginate replacement of the gelatin.

Another alginate-gelatin combination was made consisting of a replacement of the gelatin with 3 and 5% of Gm alginate. The pins were lubricated with the same lubricating grease, as well as with the same lubricating grease emulsified with a CaCl$_2$ 40% solution. SGF and SIF disintegration tests was tried on the alginate-gelatin combinations, as demonstrated in Table 11 below.

TABLE 11

| Gelatin | Alginate and Concentration (weight %) | CaCl$_2$ Emulsion | SGF Disintegration Time (min) | SIF Disintegration Time (min) |
| --- | --- | --- | --- | --- |
| FL | Mm 5% | No | 120 | 23 |
| FL | Mm 3% | No | 120 | 15 |
| FL | Gm 5% | No | 120 | 4 |
| FL | Gm 5% | Yes | 120 | 6 |
| FL | Gm 3% | No | 120 | 7 |
| FL | Gm 3% | Yes | 120 | 7 |

Additional Examples of Delayed Release Hard Shell Capsules

Delayed release hard shell capsules comprising a capsule shell comprising different alginate-gelatin combinations were made.

Trial 1

Delayed release capsules were made from a mixture comprising:

| Type B gelatin, 250 bloom, medium viscosity | 35% |
| --- | --- |
| Alginate (Mm) | 5% of the gelatin weight |
| Water | 65% |

The resulting solutions were too viscous to be used.

Trial 2

Delayed release capsules were made from a mixture comprising:

| Fish gelatin (FL) | 28.5% |
| --- | --- |
| Alginate (Mm) | 1.5% (approx. 5.2% of the gelatin weight) |
| Water | 70% |

The viscosity of the resulting solutions was acceptable. The gelatin, however, was Difficult to remove from the pins. The gelatin film was very thin, insoluble in HCl 0.1N, and insoluble in normal city water at 37 to 40° C.

Trial 3

Delayed release capsules were made from the same mixture as Trial 2. In Trial 3, the pins were greased with lubricating grease. Drying was monitored at room temperature and 35% RH. The capsule-shaped films were removed relatively easily from the pins. The body or cap was cut to the required length. The cap and body could not be joined, due to rough edges during the cutting process preventing closure and the bodies being too thick. Otherwise the capsules looked normal and could be used for testing by sealing the top with gelatin.

Trial 4

Using the same mixture as Trials 2 and 3, capsules were made at an adjusted temperature to obtain thinner films. A removal tool was used to strip the gelatin capsules from the pins. These capsules were used to test the SGF and SIF disintegration and the results are given in Table 11.

Softgel Formulation with Type B Gelatin as the Sole Gelatin Type

A softgel formulation with alkali processed, bovine hide gelatin (type BL) and high G medium viscous alginate was prepared in order to evaluate the gastro-resistance of this particular blend in simulated gastric and intestinal fluid. The following mixture was prepared:

| Gelatin (BL) | 42.6% w/w, |
| --- | --- |
| Sodium alginate (Gm) | 2.1% w/w (or 5% of the gelatin weight), |
| Glycerol | 12.8% w/w, and |
| Purified water | 42.6% w/w |

Sodium alginate was dissolved in water followed by addition of glycerol. Gelatin was then added and the mixture was left to stand for 5-10 minutes before it was melted at 80° C. The resulting solution was far too viscous to use for film casting. It was impossible to pour the solution out of the mixing beaker.

What is claimed is:

1. A delayed release capsule comprising:
    at least one agent encapsulated in a capsule shell free from any addition of calcium, wherein the capsule shell comprises:
    type A gelatin having a viscosity below 4.2 mPa·sec and/or a bloom value below 290 g; and
    alginate type M, in an amount ranging from 0.5% to 10%, by weight of the gelatin, wherein the alginate has a viscosity ranging from 420 to 600 mPa·sec.

2. The delayed release capsule according to claim 1, wherein the capsule is chosen from a sustained release capsule, a controlled release capsule, and a gastroresistant capsule.

3. The delayed release capsule according to claim 1, wherein the capsule is a soft capsule and the type A gelatin is chosen from fish gelatin, bovine gelatin, pig gelatin, and mixtures thereof.

4. The delayed release capsule according to claim 1, wherein the type A gelatin comprises fish gelatin, porcine bone, porcine skin, and mixtures thereof.

5. The delayed release capsule according to claim 1, wherein the type A gelatin has a viscosity ranging from 2.3 to 3.5 mPa·sec and a bloom value ranging from 150 g to 250 g.

6. The delayed release capsule according to claim 1, wherein the type A gelatin is present in the capsule shell in an amount ranging from 32% to 90%, relative to the weight of the capsule shell.

7. The delayed release capsule according to claim wherein the alginate type M is chosen from sodium alginate, polyethylene glycol alginate, and mixtures thereof.

8. The delayed release capsule according to claim 1, wherein the type A gelatin has a bloom value below 220 g.

9. The delayed release capsule according to claim 1, wherein the alginate type M has a viscosity ranging from 420 to 600 mPa·sec.

10. The delayed release capsule according to claim 1, wherein the delayed release capsule is a soft capsule, and the capsule shell further comprises at least one plasticizer.

11. The delayed release capsule according to claim 10, wherein the at least one plasticizer comprises from glycerol, sorbitol, trehalose, sorbitan solutions, maltitol solutions, polyethylene glycol, propylene glycol, and mixtures or combinations thereof.

12. The delayed release capsule according to claim 10, wherein the alginate and gelatin combination and the plasticizer are present at a ratio ranging in value from 1.4:1 to 5:1.

13. The delayed release capsule according to claim 1, wherein the capsule is a hard capsule, comprising type A gelatin chosen from fish and porcine gelatin,
wherein the gelatin has a viscosity below 4.2 mPa·sec and/or a bloom value of below 220 g; and the alginate is present in an amount ranging from 1% to 10%, by weight of the gelatin, said alginate type M has a viscosity of 520 mPa·sec.

14. The delayed release capsule according to claim 1, wherein the at least one agent is dissolved, dispersed, or suspended in at least one oil of vegetable or animal origin.

15. The delayed release capsule according to claim 14, wherein the at least one agent further comprises at least one suspending or solubilizing agent.

16. The delayed release capsule according to claim 15, wherein the at least one suspending or solubilizing agent is chosen from phospholipids, beeswax and other partially hydrogenated fatty acids, sorbitan esters of fatty acids, ethoxylated sorbitan esters of fatty acids, other surfactants, and mixtures thereof.

17. The delayed release capsule according to claim 1, wherein the at least one agent is dissolved, dispersed, or suspended in polyethylene glycol, mixtures of polyethelene glycols of various molecular weights, propylene glycol, polyvinylpyrrolidone, ethyl alcohol, propyl alcohol, alpha tocopheryl polyethylene glycol succinate (Vitamin E TPGS), potassium or sodium hydroxides, other alkali or acidifying agents, and mixtures thereof.

18. The delayed release capsule according to claim 1, wherein the capsule is chosen from a pharmaceutical composition, a nutritional composition, a food supplement composition herbal extracts and dietary ingredients.

19. The delayed release capsule according to claim 1, wherein the at least one agent comprises a fatty acid oil mixture comprising at least one fatty acid in a form chosen from ethyl ester, mono-, di- and triglyceride, free fatty acid, phospholipid, and combinations thereof.

20. The delayed release capsule according to claim 1, wherein the at least one agent comprises at least one omega-3 fatty acid chosen from those defined in the Pharmacopeia Omega-3 ethyl ester 90, Omega-3 ethyl ester 60, Omega-3 triglyceride 60 and fish oil monograph.

21. The delayed release capsule according to claim 1, wherein the at least one agent comprises a fatty acid oil mixture comprising from 25% to 100% of at least one fatty acid chosen from eicosapentaenoic acid (EPA) and docosahexaenoic acid (DHA) by weight, relative to the weight of the fatty acid oil mixture.

22. The delayed release capsule according to claim 21, wherein the fatty acid oil mixture is derived from at least one oil chosen from marine oil, algae oil, plant-based oil, and microbial oil.

23. The delayed release capsule according to claim 13, wherein the at least one agent further comprises at least one other pharmaceutical active ingredient or a nutritional ingredient in the form of powders, beadlets or granules other than a fatty acid oil mixture.

24. The delayed release capsule according to claim 1, wherein the type A gelatin has a viscosity below 4.2 mPa·sec and/or a bloom value ranging from 60 g to 180 g, and comprises at least one of pig bone and pig skin, and the alginate type M is present in an amount of 1% to 5% by weight of the gelatin has a viscosity of 520 mPa·sec, wherein the delayed release capsule is a soft capsule, and the capsule shell encapsulates:
at least one fatty acid oil mixture comprising from 30% to 100% of at least one fatty acid chosen from eicosapentaenoic acid (EPA) and/or docosahexaenoic acid (DHA), by weight of the fatty acid oil mixture, wherein the EPA and DHA are in a form chosen from ethyl ester and triglyceride;
at least one vitamin, mineral, or both, fatty acid oil mixture of plant, animal or microbial, a probiotic product, either plant or microbial;
at least one film-enrobed unitary core product or multiple solid dosage forms in the form of beadlets or granules.

* * * * *